US011098066B2

(12) United States Patent
Rölle et al.

(10) Patent No.: US 11,098,066 B2
(45) Date of Patent: *Aug. 24, 2021

(54) METHOD FOR PRODUCING TRIARYLORGANOBORATES

(71) Applicant: Covestro Deutschland AG, Leverkusen (DE)

(72) Inventors: Thomas Rölle, Leverkusen (DE); Horst Berneth, Leverkusen (DE); Dennis Hönel, Zülpich-Wichterich (DE); Friedrich-Karl Bruder, Krefeld (DE); Jürgen Kintrup, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 11 days.

This patent is subject to a terminal disclaimer.

(21) Appl. No.: 16/348,309

(22) PCT Filed: Nov. 7, 2017

(86) PCT No.: PCT/EP2017/078415
§ 371 (c)(1),
(2) Date: May 8, 2019

(87) PCT Pub. No.: WO2018/087064
PCT Pub. Date: May 17, 2018

(65) Prior Publication Data
US 2019/0263838 A1    Aug. 29, 2019

(30) Foreign Application Priority Data

Nov. 9, 2016  (EP) .................................. 16197990
Aug. 24, 2017 (EP) .................................. 17187666

(51) Int. Cl.
| C07F 5/00 | (2006.01) |
| C07C 271/00 | (2006.01) |
| C07C 219/00 | (2006.01) |
| C07C 217/00 | (2006.01) |
| C07C 211/00 | (2006.01) |
| C07F 5/02 | (2006.01) |
| C07C 211/63 | (2006.01) |
| C07C 211/64 | (2006.01) |
| C07C 217/08 | (2006.01) |
| C07C 219/10 | (2006.01) |
(Continued)

(52) U.S. Cl.
CPC ............ *C07F 5/027* (2013.01); *C07C 211/63* (2013.01); *C07C 211/64* (2013.01); *C07C 217/08* (2013.01); *C07C 219/10* (2013.01); *C07C 219/28* (2013.01); *C07C 219/30* (2013.01); *C07C 271/12* (2013.01); *C07C 271/16* (2013.01); *C07C 271/20* (2013.01); *C07C 271/24* (2013.01); *C07C 271/28* (2013.01); *C07D 213/20* (2013.01); *C07D 233/02* (2013.01); *C07D 233/58* (2013.01); *C07D 247/00* (2013.01); *C07D 295/037* (2013.01); *C07D 309/34* (2013.01); *C07D 335/02* (2013.01); *C07D 347/00* (2013.01); *C07D 413/06* (2013.01); *C07F 5/04* (2013.01); *C07F 9/54* (2013.01); *C07F 9/5407* (2013.01); *C07F 9/5442* (2013.01); *G03F 7/001* (2013.01); *C07C 2601/14* (2017.05)

(58) Field of Classification Search
CPC ..... C07F 5/027; C07C 271/28; C07C 271/16; C07C 211/63; C07C 211/64; C07C 217/08; C07C 219/10; C07C 219/28; C07C 219/30; C07C 271/20; C07C 271/24; C07C 2601/14
See application file for complete search history.

(56) References Cited

U.S. PATENT DOCUMENTS

| 2,857,310 A | 10/1958 | Heininger |
| 3,125,555 A | 3/1964 | Paré et al. |

(Continued)

FOREIGN PATENT DOCUMENTS

| DE | 3723797 A1 | 1/1989 |
| DE | 19850139 A1 | 5/1999 |

(Continued)

OTHER PUBLICATIONS

International Search Report for PCT/EP2017/078412 dated Mar. 20, 2018.
International Search Report for PCT/EP2017/078415 dated Jan. 3, 2018.
International Search Report for PCT/EP2017/078416 dated Jan. 4, 2018.
Written Opinion of the International Searching Authority for PCT/EP2017/078412 dated Mar. 20, 2018.
Written Opinion of the International Searching Authority for PCT/EP2017/078415 dated Jan. 3, 2018.
Written Opinion of the International Searching Authority for PCT/EP2017/078416 dated Jan. 4, 2018.
U.S. Appl. No. 16/348,262, filed May 9, 2019.

(Continued)

*Primary Examiner* — Sikarl A Witherspoon
(74) *Attorney, Agent, or Firm* — Faegre Drinker Biddle & Reath LLP

(57) ABSTRACT

Provided herein is a process for preparing triaryl organoborates of the formula $1/n\ K^{n+}R_3^4B^- - R^1$ (IV), where one equivalent of organoboronic ester of the formula $B-R^1(OR^2)(OR^3)$ (I) is initially charged together with $1/n$ equivalents of salt $K^{n+}\ nX^-$ (II) and 3 equivalents of metal M in a solvent or a solvent mixture S1, 3 equivalents of a haloaromatic $R^4-Y$ (III) are added, an auxiliary L and optionally a second organic solvent or solvent mixture S2 is added and the compound $1/n\ K^{n+}\ R_3^4B^- - R^1$ (IV) is separated off with the organic phase, and to the use of these substances as co-initiator in photopolymer formulations.

12 Claims, 1 Drawing Sheet

(51) Int. Cl.

| | | |
|---|---|---|
| *C07C 219/28* | (2006.01) | |
| *C07C 219/30* | (2006.01) | |
| *C07C 271/12* | (2006.01) | |
| *C07C 271/20* | (2006.01) | |
| *C07C 271/24* | (2006.01) | |
| *C07D 213/20* | (2006.01) | |
| *C07D 233/58* | (2006.01) | |
| *C07D 295/037* | (2006.01) | |
| *C07D 413/06* | (2006.01) | |
| *C07F 5/04* | (2006.01) | |
| *C07F 9/54* | (2006.01) | |
| *G03F 7/00* | (2006.01) | |
| *C07C 271/28* | (2006.01) | |
| *C07D 347/00* | (2006.01) | |
| *C07D 233/02* | (2006.01) | |
| *C07D 247/00* | (2006.01) | |
| *C07D 335/02* | (2006.01) | |
| *C07C 271/16* | (2006.01) | |
| *C07D 309/34* | (2006.01) | |

(56) References Cited

U.S. PATENT DOCUMENTS

| | | | |
|---|---|---|---|
| 4,076,756 | A | 2/1978 | Nazarenko et al. |
| 4,954,635 | A | 9/1990 | Rosario-Jansen et al. |
| 4,970,217 | A | 11/1990 | Prücher et al. |
| 5,151,520 | A | 9/1992 | Gottschalk et al. |
| 5,194,472 | A | 3/1993 | Wilson et al. |
| 5,565,290 | A | 10/1996 | Itakura et al. |
| 6,096,794 | A | 8/2000 | Cunningham et al. |
| 6,140,537 | A * | 10/2000 | Katoh .................. C07F 9/54 546/13 |
| 9,146,456 | B2 | 9/2015 | Berneth et al. |
| 9,754,084 | B2 | 9/2017 | Rölle et al. |
| 9,804,490 | B2 | 10/2017 | Rölle et al. |
| 10,001,703 | B2 | 6/2018 | Berneth et al. |
| 2016/0320695 | A1 | 11/2016 | Rölle et al. |
| 2019/0276479 | A1 | 9/2019 | Rolle et al. |

FOREIGN PATENT DOCUMENTS

| | | |
|---|---|---|
| EP | 0223587 A1 | 5/1987 |
| GB | 2307474 A | 5/1997 |
| JP | 11-269210 A | 10/1999 |
| JP | 200123381 A | 1/2001 |
| JP | 2001233881 A | 8/2001 |
| JP | 2002226486 A | 8/2002 |
| JP | 2009029857 A | 2/2009 |
| JP | 2012211938 A | 11/2012 |
| SK | 278487 B6 | 7/1997 |
| WO | WO-2000030444 A1 | 6/2000 |
| WO | WO-2012062655 A2 | 5/2012 |
| WO | WO-2014053408 A1 | 4/2014 |
| WO | WO-2015055576 A1 | 4/2015 |
| WO | WO-2015091427 A1 | 6/2015 |
| WO | WO-2015187766 A1 | 12/2015 |
| WO | WO-2018087062 A1 | 5/2018 |

OTHER PUBLICATIONS

U.S. Appl. No. 16/348,333, filed May 9, 2019.
Howell, B., et al., "Pigmented Coatings Cured and Visibile Light", Photopolymerization, 1997, Chapter 16, pp. 219-232.
Sarker, A., et al., Visible Light Photopolymerization Employing 2,4 Diiodo-6-butoxy-3-fluorone and Tetraorganylborate Salts as Photoinitiators, Journal of Polymer Science: Part A: Polymer Chemistry, 1996, vol. 34, pp. 2817-2824.
International Preliminary Report on Patentability received for PCT Patent Application No. PCT/EP2017/078415, dated May 23, 2019, 28 pages (17 pages of English Translation and 11 pages of Original Document).

* cited by examiner

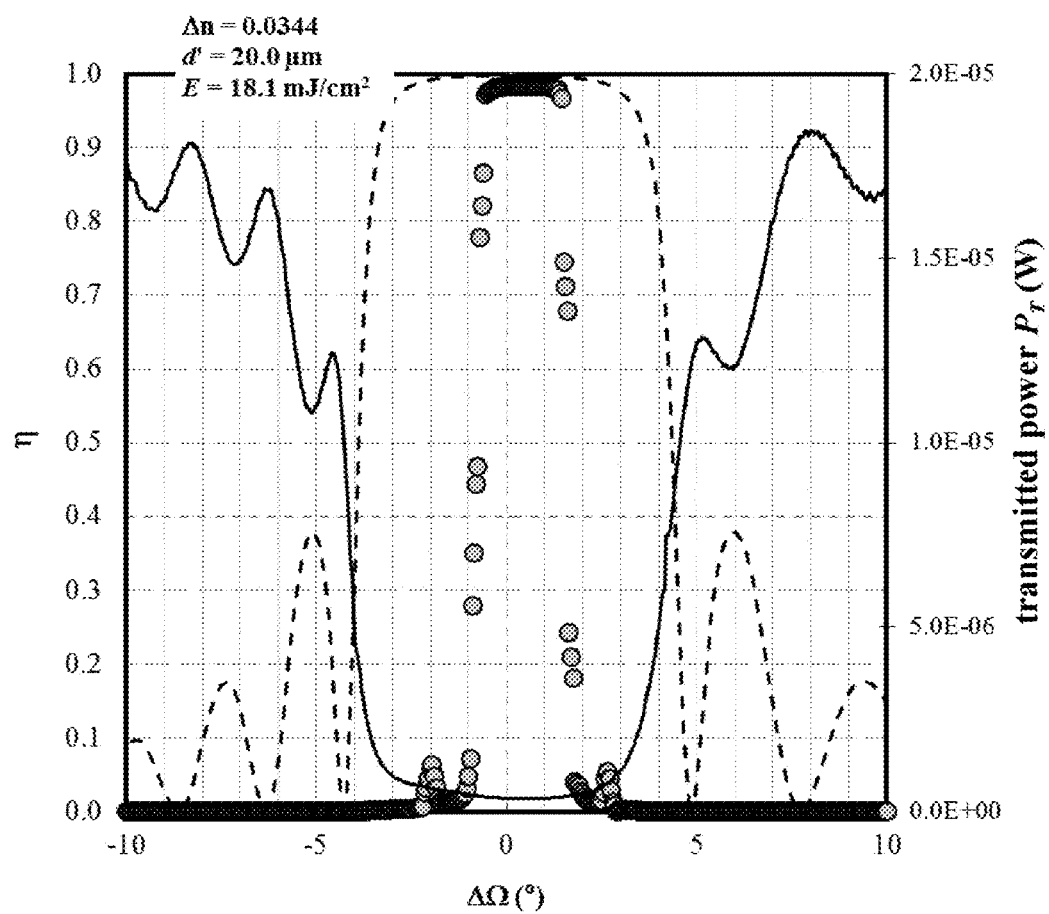

METHOD FOR PRODUCING TRIARYLORGANOBORATES

CROSS-REFERENCE TO RELATED APPLICATIONS

This application is a national stage application (under 35 U.S.C. § 371) of PCT/EP2017/078415, filed Nov. 7, 2017, which claims benefit of European Application Nos. 16197990.1, filed Nov. 9, 2016, and 17187666.7, filed Aug. 24, 2017 all of which are incorporated herein by reference in their entirety.

The invention relates to a process for preparing triaryl organoborates proceeding from organoboronic esters in the presence of an n-valent cation $1/n\ K^{n+}$, comprising the anhydrous workup of the reaction mixture and the use of the triaryl organoborates obtained as co-initiator in photopolymer formulations, holographic media and holograms.

Triaryl organoborates, together with suitable sensitizers, for example cationic, anionic or uncharged dyes, can form type (II) photoinitiators that trigger free-radical photopolymerization of suitable monomers via actinic radiation. The preparation thereof has been widely described, and selected tetraalkylammonium triaryl(alkyl)borates are commercially available.

DE 198 50 139 A1 describes the synthesis of tetraalkylammonium triaryl(alkyl)borates proceeding from an alkyl or cycloalkyl boronate, and the reaction thereof with three equivalents of an organometallic reagent, especially a Grignard reagent. In a first step, the alkyl or cycloalkyl boronate is prepared and isolated, and this alkyl or cycloalkyl boronate is then reacted with a separately prepared organometallic reagent, generally a Grignard reagent. In a third step, the triaryl(alkyl)borate thus formed is precipitated in salt form by addition of a tetrealkylammonium compound and purified, for example by crystallization. There are thus a total of 3 synthesis stages for preparation of tetraalkylammonium triaryl(alkyl)borates. Since the solubility of organometallic reagents, especially Grignard reagents, in the ethereal solvents that are typically used is limited, it is necessary in this process, especially at the organometallic reagent stage, to work in quite dilute solution in order to keep all the ingredients homogeneously in solution. The solubility of Grignard reagents in tetrahydrofuran or diethyl ether, which are the ethers typically used, is typically 1 to 2 mol per litre. Since, however, three equivalents of Grignard reagent are required owing to the stoichiometry, the target concentration of product is one third of this value, meaning that the solubility of the Grignard reagent defines the target concentration. An optimized space-time yield is an important aim for industrial application. However, this can be achieved only to a limited degree by the process described in DE 198 50 139 A1.

JP2002-226486 A describes the synthesis of ammonium and phosphonium triaryl(alkyl)borates proceeding from an alkyl or cycloalkyl boronate and the reaction thereof with three equivalents of an organometallic reagent, especially a Grignard reagent, by an in situ method (Barbier), in which the organometallic reagent is generated in the presence of the electrophilic alkyl or cycloalkyl boronate. In this way, it is possible to achieve higher space-time yields, and the exothermicity of the organometallic stage can thus be better controlled. Furthermore, some reactive organometallic reagents are only of limited storage stability and have to be protected from water or atmospheric oxygen at great cost and inconvenience, since they are otherwise hydrolysed or oxidized, which in turn reduces the overall yield.

However, both processes described above still require the addition of the selected cation in a further reaction step. It is advantageous for an economically viable preparation on the industrial scale when the cation chosen is already present in the preparation of the triaryl organoborate, because a further reaction step is thus dispensed with and the procedure and workup can be made more efficient. Moreover, the concentration of the reagents can be increased further, since the metal-arylammonium salts that otherwise occur in the solvents used are only of limited solubility and prevent control over the reaction enthalpy through voluminous precipitates.

The problem addressed by the present invention was therefore that of providing a process for preparing triaryl organoborates, in which an improved space-time yield leads to better economic viability.

This object was achieved in accordance with the invention by a process for preparing triaryl organoborates of the formula $1/n\ K^{n+}R_3^4B^-\!\!-\!\!R^1$ (IV), where one equivalent of organoboronic ester of the formula $B\!\!-\!\!R^1(OR^2)(OR^3)$ (I) is initially charged together with $1/n$ equivalents of salt $K^{n+}nX^-$ (II) and 3 equivalents of metal M in a solvent or a solvent mixture S1, 3 equivalents of a haloaromatic $R^4\!\!-\!\!Y$ (III) are added, an auxiliary L and optionally a second organic solvent or solvent mixture S2 is added and the compound $1/n\ K^{n+}R_3^4B^-\!\!-\!\!R^1$ (IV) is separated off with the organic phase and $R^1$ is an optionally hydroxyl- and/or alkoxy- and/or acyloxy- and/or halogen-substituted $C_1$- to $C_{22}$-alkyl, $C_3$- to $C_{22}$-alkenyl, $C_3$- to $C_{22}$-alkynyl, $C_5$- to $C_7$-cycloalkyl or $C_7$- to $C_{13}$-aralkyl radical, $R^2$ and $R^3$ are independently an optionally branched $C_1$- to $C_{22}$-alkyl radical or an optionally alkyl-substituted $C_3$- to $C_7$-cycloalkyl radical or $R^2$ and $R^3$ together form a 2-8-membered carbon bridge which is optionally substituted by alkyl and/or interrupted by oxygen atoms, $R^4$ is a $C_6$- to $C_{10}$-aryl radical optionally substituted by at least one radical selected from halogen, $C_1$- to $C_4$-alkyl, trifluoromethyl, $C_1$- to $C_4$-alkoxy, trifluoromethoxy, phenyl and phenoxy, K is an organocation of valency n and having any substitution, based on nitrogen, phosphorus, oxygen, sulfur and/or iodine, and L is an auxiliary that forms a complex of sparing solubility in S1 and/or S2 with M salts $MY(OR^2)$, $MY(OR^3)$ and MXY, where L is a Lewis-basic compound, especially selected from the group consisting of open chain or cyclic or polycyclic ethers or polyethers or (poly)ether polyols, amine-functionalized and/or alkylamine-functionalized alcohols or polyols or (poly)ether polyols, weakly basic organic compounds, weakly acidic macroporous cation exchangers and weakly alkaline macroporous cation exchangers, M is any metal selected from the alkali metals, magnesium, calcium and aluminium, X is a halide or alkoxide or alkyl sulfide, Y is iodine or bromine or chlorine, n is 1, 2 or 3, S1 is an aprotic organic solvent or a mixture of aprotic solvents and S2 is an aprotic organic solvent or a mixture of aprotic solvents.

In this process, addition of 3 equivalents of a haloaromatic $R^4\!\!-\!\!Y$ (III) to the 3 equivalents of metal initially charged results in in situ generation of an organometallic reagent that reacts with the initially charged substances (I) and (II) to give the $1/n\ K^{n+}R_3^4B^-\!\!-\!\!R^1$ organoborate (IV). It has been found that, surprisingly, the use of substituted organocations of valency n based on nitrogen, phosphorus, oxygen, sulfur and/or iodine as cations has an advantageous effect on the reaction, since they are chemically inert and the reaction proceeds with a higher space-time yield than known processes and fewer side reactions occur and hence the yield is increased and a higher purity of the target product is very much more easily achievable.

Also found to be advantageous is the workup of the reaction mixture by addition of an auxiliary L which forms a complex with the M salts $MY(OR^2)$, $MY(OR^3)$ and MXY, and optionally of a further solvent or solvent mixture S2. Through suitable choice of L and S1 and/or S2, sparingly soluble complexes are thus obtained, which can be separated in a simple manner by suitable processes, for example decantation, filtration, centrifugation or the like, from the desired triaryl organoborates of the formula $1/n\ K^{n+}R_3{}^4B^-\!\!-\!\!R^1$ (IV) that are dissolved in the organic phase.

The inventive triaryl organoborates of formula IV are preferably triaryl(alkyl)borates, triaryl(cycloalkyl)borates, triaryl(alkenyl)borates, triaryl(alkynyl)borates and/or triaryl (aralkyl)borates, more preferably triaryl(alkyl)borates and/or triaryl(cycloalkyl)borates.

The invention therefore likewise provides a process for preparing compounds $1/n\ K^{n+}R_3{}^4B^-\!\!-\!\!R^1$ of the formula IV, comprising the steps of i) initially charging one equivalent of organoboronic ester $B\!\!-\!\!R^1(OR^2)(OR^3)$ (I) together with $1/n$ equivalents of salt $K^{n+}\ nX^-$ (II) and 3 equivalents of metal M in a solvent or solvent mixture S1, ii) adding 3 equivalents of a haloaromatic $R^4\!\!-\!\!Y$ (III), as a result of which iii) an organometallic reagent generated in situ reacts with the initially charged substances (I) and (II) to give $1/n\ K^{n+}R_3{}^4B^-\!\!-\!\!R^1$ (IV), iv) adding an auxiliary L and v) optionally a second organic solvent S2, where the compound $1/n\ K^{n+}R_3{}^4B^-\!\!-\!\!R^1$ (IV) remains in the organic phase, and vi) the metal salts $MY(OR^2)$, $MY(OR^3)$ and MXY are separated off as precipitated solid complexes $MY(OR^2)$L, $MY(OR^3)$L and MXYL.

This reaction conforms to the following reaction scheme:

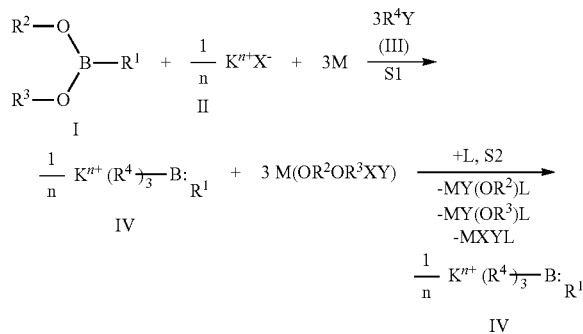

Preferably, $R^1$ is an optionally hydroxyl- and/or alkoxy- and/or acyloxy- and/or halogen-substituted $C_2$- to $C_{18}$-alkyl, $C_3$- to $C_{18}$-alkenyl, $C_3$- to $C_{18}$-alkynyl, $C_5$- to $C_6$-cycloalkyl or $C_7$- to $C_{13}$-aralkyl radical and, more preferably, $R^1$ is an optionally hydroxyl- and/or alkoxy- and/or acyloxy- and/or halogen-substituted $C_4$- to $C_{16}$-alkyl, $C_3$- to $C_{16}$-alkenyl, $C_3$- to $C_{16}$-alkynyl, cyclohexyl or $C_7$- to $C_{13}$-aralkyl radical.

Preferably, $R^2$ and $R^3$ are independently an optionally branched $C_2$- to $C_{18}$-alkyl radical or $R^2$ and $R^3$ together form a 4-7-membered, optionally substituted carbocycle and, more preferably, $R^2$ and $R^3$ are independently an optionally branched $C_3$- to $C_{12}$-alkyl radical or $R^2$ and $R^3$ together form a 4-6-membered, optionally substituted carbocycle.

Preferably, $R^4$ is a $C_6$- to $C_{10}$-aryl radical optionally substituted by at least one radical selected from halogen, $C_1$- to $C_4$-alkyl, trifluoromethyl, $C_1$- to $C_4$-alkoxy, trifluoromethoxy, phenyl and/or phenoxy and, more preferably, $R^4$ is a $C_6$-aryl radical optionally substituted by at least one radical selected from halogen, $C_1$- to $C_4$-alkyl, trifluoromethyl, $C_1$- to $C_4$-alkoxy, trifluoromethoxy, phenyl and/or phenoxy.

An organocation K of valency n based on nitrogen and having any substitution is understood to mean, for example, ammonium ions, pyridinium ions, pyridazinium ions, pyrimidinium ions, pyrazinium ions, imidazolium ions, 1H-pyrazolium ions, 3H-pyrazolium ions, 4H-pyrazolium ions, 1-pyrazolinium ions, 2-pyrazolinium ions, 3-pyrazolinium ions, imidazolinium ions, thiazolium ions, 1,2,4-triazolium ions, 1,2,3-triazolium ions, pyrrolidinium ions, quinolinium ions, which optionally bear further functional groups such as ethers, esters, amides and/or carbamates in one or more side chains and which may also be in oligomeric or polymeric or bridging form. Preferred organocations K of valency n based on nitrogen are, for example, ammonium ions, pyridinium ions, pyridazinium ions, pyrimidinium ions, pyrazinium ions, imidazolium ions, pyrrolidinium ions, which optionally bear further functional groups such as ethers, esters, amides and/or carbamates in one or more side chains and which may also be in oligomeric or polymeric or bridging form. Particularly preferred organocations K of valency n based on nitrogen are, for example, ammonium ions, pyridinium ions and imidazolium ions, which optionally bear further functional groups such as ethers, esters, amides and/or carbamates in one or more side chains and which may also be in oligomeric or polymeric or bridging form. Polymeric cations may also be included within the meaning of the abovementioned substitution patterns.

An organocation K of valency n based on phosphorus and having any substitution is understood to mean, for example, phosphorus(IV) compounds of coordination number 4, for example tetraalkylphosphonium, trialkylarylphosphonium, dialkyldiarylphosphonium, alkyltriarylphosphonium, or tetraarylphosphonium salts having any substitution, which optionally bear further functional groups such as ethers, esters, carbonyls, amides and/or carbamates in one or more side chains and which may also be in oligomeric or polymeric or bridging form. Likewise encompassed are 5- to 8-membered aliphatic, quasi-aromatic or aromatic cyclic compounds containing 1, 2 or 3 phosphonium(IV) atoms which may then be substituted by any alkyl or aryl substituents to establish the tetravalency of the phosphorus atom. Aromatic radicals may additionally bear any number of halogen atoms or nitro, cyano, trifluoromethyl, ester and/or ether substituents. It is of course possible for the alkyl and aryl radicals to be bridged to one another by carbon chains or mono- and/or polyether chains, and these then form mono- or polycyclic structures. Preferred organocations K of valency n based on phosphorus are, for example, tetraalkylphosphonium, trialkylarylphosphonium, alkyltriarylphosphonium, dialkyldiarylphosphonium or tetraarylphosphonium salts having any substitution, which optionally bear further functional groups such as carbonyls, amides and/or carbamates in one or more side chains and which may also be in oligomeric or polymeric or bridging form. Aromatic radicals may additionally bear any number of halogen atoms or ester and/or ether substituents. It is of course possible for the alkyl and aryl radicals to be bridged to one another by carbon chains or mono- and/or polyether chains, and these then form mono- or polycyclic structures. Particularly preferred organocations K of valency n based on phosphorus are, for example, tetraalkylphosphonium, trialkylarylphosphonium, dialkyldiarylphosphonium, alkyltriarylphosphonium or tetraarylphosphonium salts having any substitution, which optionally bear further functional groups such as carbonyls, amides and/or carbamates in one or more side chains and which may also be in oligomeric or polymeric or bridging form. Aromatic radicals may additionally bear any number of halogen atoms. It is of course possible for the alkyl and aryl radicals to be bridged to one another by carbon chains or mono- and/or polyether chains, and these then form mono- or polycyclic structures. Polymeric cations as specified, for example, in U.S. Pat. No. 3,125,555 may be included within the meaning of the abovementioned substitution patterns.

An organocation K of valency n based on oxygen and having any substitution is understood to mean, for example, pyrylium having any substitution, including in fused form as in benzopyrylium, flavylium naphthoxanthenium. Preferred organocations K of valency n based on oxygen and having any substitution are, for example, pyrylium having any substitution, including in fused form as in benzopyrylium, flavylium. Polymeric cations may also be included within the meaning of the abovementioned substitution patterns.

An organocation K of valency n based on sulfur and having any substitution is understood to mean onium compounds of sulfur that bear identical or different optionally substituted $C_1$- to $C_{22}$-alkyl, $C_6$- to $C_{14}$-aryl, $C_7$- to $C_{15}$-arylalkyl or $C_5$- to $C_7$-cycloalkyl radicals and/or that form oligomeric or polymeric repeating connecting units to give sulfonium salts with $1 \leq n \leq 3$. Likewise encompassed are 5- to 8-membered aliphatic, quasi-aromatic or aromatic cyclic compounds containing 1 or 2 sulfonium(III) atoms which may then be substituted by any alkyl or aryl substituents to establish the trivalency of the sulfur atom. Preferred organocations K of valency n based on sulfur are onium compounds of sulfur that bear identical or different optionally substituted $C_4$- to $C_{14}$-alkyl, $C_6$- to $C_{10}$-aryl, $C_7$- to $C_{12}$-arylalkyl or $C_5$- to $C_6$-cycloalkyl radicals and/or that form oligomeric or polymeric repeating connecting units to give sulfonium salts with $1 \leq n \leq 3$, and also thiopyrylium. Particularly preferred organocations K of valency n based on sulfur are onium compounds of sulfur that bear identical or different optionally substituted $C_6$- to $C_{12}$-alkyl, $C_6$- to $C_{10}$-aryl, $C_7$- to $C_{12}$-arylalkyl or $C_5$- to $C_6$-cycloalkyl radicals and/or that form oligomeric or polymeric repeating connecting units to give sulfonium salts with $1 \leq n \leq 3$, and also thiopyrylium. Polymeric cations may also be included within the meaning of the abovementioned substitution patterns.

An organocation K of valency n based on iodine and having any substitution is understood to mean onium compounds of iodine that bear identical or different optionally substituted $C_1$- to $C_{22}$-alkyl, $C_6$- to $C_{14}$-aryl, $C_7$- to $C_{15}$-arylalkyl or $C_5$- to $C_7$-cycloalkyl radicals and/or that form oligomeric or polymeric repeating connecting units to give iodonium salts with $1 \leq n \leq 3$. Preferred organocations K of valency n based on iodine are onium compounds of iodine that bear identical or different optionally substituted $C_4$- to $C_{14}$-alkyl, $C_6$- to $C_{10}$-aryl, $C_7$- to $C_{12}$-arylalkyl or $C_5$- to $C_6$-cycloalkyl radicals and/or that form oligomeric or polymeric repeating connecting units to give iodonium salts with $1 \leq n \leq 3$. Particularly preferred organocations K of valency n based on iodine are onium compounds of iodine that bear identical or different optionally substituted $C_4$- to $C_{12}$-alkyl, $C_6$- to $C_{10}$-aryl, $C_7$- to $C_{12}$-arylalkyl or $C_5$- to $C_6$-cycloalkyl radicals and/or that form oligomeric or polymeric repeating connecting units to give iodonium salts with $1 \leq n \leq 3$. Polymeric cations may also be included within the meaning of the abovementioned substitution patterns.

An auxiliary L that forms a complex of sparing solubility in the solvent or solvent mixture S1 and/or S2 with metal salts $MY(OR^2)$, $MY(OR^3)$ and MXY is understood to mean Lewis-basic compounds which may be in liquid or solid or polymer-bound form (the term "Lewis base" according to p. 1136 in Pure & Appl. Chem., 66 (5), 1077-1184, 1994). This auxiliary is added in place of the otherwise standard aqueous workup after the end of the reaction and forms a solid removable by filtration with the metal salts $MY(OR^2)$, $MY(OR^3)$ and MXY. Examples of such auxiliaries L are open-chain or cyclic or polycyclic ethers or polyethers or (poly)ether polyols such as 1,4-dioxane or ethane-1,2-diol. It is likewise possible to use amine- and/or alkylamine-functionalized alcohols, polyols or (poly)ether polyols such as aminoethanol, methylaminoethanol or dimethylaminoethanol. It is also possible to use weakly acidic or weakly alkaline macroporous cation exchangers, some of which have been developed selectively for the complexation of alkaline earth metal ions. In addition, it is possible to use weakly basic organic compounds such as pyridine, 2,6-dimethylpyridine, triethylamine, diisopropylethylamine or coordinating compounds such as triphenylphosphine, tri(o-tolyl)phosphine. It is of course also possible to use mixtures of auxiliaries. The auxiliaries may additionally be added in a substoichiometric, stoichiometric or superstoichiometric ratio. The contact time of the auxiliary may be of any length, preferably <24 h, more preferably <12 h, especially preferably <1 h and exceptionally preferably <0.1 h. In a preferred embodiment, the auxiliary L is a Lewis-basic compound selected from the group consisting of open chain or cyclic or polycyclic ethers or polyethers or (poly)ether polyols, amine-functionalized and/or alkylamine-functionalized alcohols or polyols or (poly)ether polyols, weakly basic organic compounds, weakly acidic macroporous cation exchangers and weakly alkaline macroporous cation exchangers. In a further preferred embodiment, the auxiliary L comprises Lewis-basic compounds having at least one freely available coordination site or mixtures thereof, preferably selected from the group consisting of open-chain or cyclic or polycyclic ethers or polyethers or (poly)ether polyols, amine- and/or alkylamine-functionalized alcohols or polyols or (poly)ether polyols, weakly basic organic compounds, weakly acidic macroporous cation exchangers and weakly alkaline macroporous cation exchangers, more preferably selected from the group consisting of cyclic ethers or polyethers or (poly)ether polyols, weakly acidic macroporous cation exchangers and weakly alkaline macroporous cation exchangers, even more preferably selected from the group consisting of cyclic ethers, weakly acidic macroporous cation exchangers and weakly alkaline macroporous cation exchangers.

An aprotic organic solvent or a mixture of aprotic organic solvents S1 is understood to mean solvents that are not deprotonatable without strong bases (Reichardt, C., Solvents and Solvent Effects in Organic Chemistry, 3rd ed.; Wiley-VCH: Weinheim, (2003)). Examples of aprotic organic solvents S1 are alkanes, alkenes, alkynes, benzene and aromatics having aliphatic and/or aromatic substituents, carboxylic esters and/or ethers. Preferred aprotic organic solvents S1 are alkanes, aromatics having aliphatic and/or aromatic substituents and/or ethers. Examples of those used include aromatic hydrocarbons such as solvent naphtha, toluene or xylene, or ethers such as tetrahydrofuran, methyltetrahydrofuran, diethyl ether or dimethoxyethane. The solvent should be very substantially anhydrous. In a preferred embodiment, the solvent or solvent mixtures S1 is/are different from the auxiliary L, meaning that S1 and L are not the same substance.

An aprotic organic solvent or a mixture of aprotic organic solvents S2 is understood to mean solvents that are not deprotonatable without strong bases (Reichardt, C., Solvents and Solvent Effects in Organic Chemistry, 3rd ed.; Wiley-VCH: Weinheim, (2003)). Examples of aprotic organic solvents S2 are alkanes, alkenes, alkynes, benzene and aromatics having aliphatic and/or aromatic substituents, carboxylic esters and/or ethers. Preferred aprotic organic solvents S2 are alkanes, aromatics having aliphatic and/or aromatic substituents and/or carboxylic esters. Examples of those used include aromatic hydrocarbons such as solvent naphtha, toluene or xylene, or esters such as methyl acetate, ethyl acetate, butyl acetate, methoxypropyl acetate or propylene glycol diacetate. In a preferred embodiment, the solvent or solvent mixtures S2 is/are different from the auxiliary L, meaning that S2 and L are not the same substance.

Preferably, M is magnesium, calcium or aluminium and, more preferably, M is magnesium.

Preferably, X is a halide or alkoxide, X is more preferably a halide and X is especially preferably chloride or bromide.

Preferably, Y is bromine or chlorine and, more preferably, Y is bromine.

Preferably, n is 1 or 2 and, more preferably, n is 1.

In the context of the invention, $C_1$-$C_{22}$-alkyl is, for example, methyl, ethyl, n-propyl, isopropyl, n-butyl, sec-butyl, tert-butyl, n-pentyl, 1-methylbutyl, 2-methylbutyl, 3-methylbutyl, neopentyl, 1-ethylpropyl, 1,1-dimethylpropyl, 1,2-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl, n-heptyl, n-octyl, 2-ethylhexyl, pinacyl, n-nonyl, n-decyl, n-dodecyl, n-tridecyl, n-tetradecyl, n-hexadecyl, n-octadecyl, n-eicosyl, n-docosyl. The same applies to the corresponding alkyl radical, for example in aralkyl/alkylaryl, alkylphenyl or alkylcarbonyl radicals. Alkyl radicals, alkenyl radicals or alkynyl radicals in the corresponding hydroxyalkyl or aralkyl/alkylaryl radicals are, for example, the alkyl radicals, alkenyl radicals or alkynyl radicals corresponding to the preceding alkyl radicals.

Examples are 2-chloroethyl, benzyl, allyl, 2-buten-1-yl, propargyl.

In the context of the invention, cycloalkyl is, for example, cyclopropyl, cyclobutyl, cyclopentyl, cyclohexyl, cycloheptyl, adamantyl or the isomeric menthyls.

Aryl is a carbocyclic aromatic radical having 6 to 14 skeletal carbon atoms. The same applies to the aromatic moiety of an arylalkyl radical, also known as an aralkyl radical, and to aryl constituents of more complex groups, for example arylcarbonyl radicals.

Alkylene is a diradical of a saturated branched or unbranched hydrocarbon, for example methylene (—$CH_2$—), ethylene (—$CH_2CH_2$—), propylene (—$CH_2CH_2CH_2$—) etc.

Cyclopentylene is a diradical of an optionally alkyl-substituted cyclopentane ring.

Cyclohexylene is a diradical of an optionally alkyl-substituted cyclohexane ring.

Cycloheptylene is a diradical of an optionally alkyl-substituted cycloheptane ring.

Aryldialkylene is a diradical of a saturated branched or unbranched alkylarylalkyl, where the aryl ring may optionally be substituted by alkyl, aryl, halogen, for example xylylene (1,2- or 1,3- or 1,4-phenylenebis(methylene)).

Arylene is a diradical of an aryl.

Heteroarylene is a diradical of a heteroaryl.

Alkylene-cycloalkylene is a diradical of an alkylcycloalkane, bonded to a first radical on one side via the alkyl group and bonded to a second radical via the cycloalkyl group.

Alkanedicycloalkylene is a diradical of a dicycloalkylalkane, for example methylenebis(cyclohexane-4,1-diyl).

Alkanediarylene is a diradical of a diarylalkane, for example 4-methylenebis(4,1-phenylene).

Examples of $C_6$- to $C_{14}$-aryl are phenyl, o-, p-, m-tolyl, o-, p-, m-ethylphenyl, naphthyl, phenanthrenyl, anthracenyl, fluorenyl, o-, p-, m-fluorophenyl, o-, p-, m-chlorophenyl, o-, p-, m-methoxyphenyl, o-, p-, m-trifluoromethylphenyl, o-, p-, m-trifluoromethoxyphenyl, o-, m- or p-biphenylyl, o-, p-, m-phenoxyphenyl, 3,4-dimethylphenyl, 3,4-dichlorophenyl, 3,4-difluorophenyl, 3,4-dimethoxyphenyl, 4-methyl-3-fluorophenyl, 4-methyl-3-chlorophenyl, 3,4,5-trifluorophenyl. Arylalkyl and aralkyl are each independently a straight-chain, cyclic, branched or unbranched alkyl radical as defined above, which may be mono-, poly- or persubstituted by aryl radicals as defined above.

Examples are benzyl, 4-chlorobenzyl, phenethyl, 2-phenyl-1-propyl, 3-phenyl-1-propyl, 1-phenyl-2-propyl, diphenylmethyl.

Examples of a 2-8-membered carbon bridge optionally substituted by alkyl and/or interrupted by oxygen atoms are —$CH_2$—$CH_2$—, —$CH_2$—$CH_2$—$CH_2$—, —$CH_2$—$CH_2$—$CH_2$—$CH_2$—, —$CH_2$—$CH_2$—O—$CH_2$—$CH_2$—, —$CH_2$—$CH(CH_3)$—.

Examples of a 4-14-membered carbon tricycle optionally substituted by alkyl or aryl and/or interrupted by oxygen atoms are:

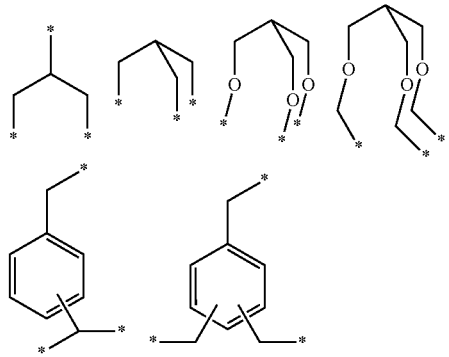

The reaction is generally executed without employment of elevated pressure. In that case, the pressure employed in practice will thus at least be the autogenous pressure.

The reaction is generally conducted at temperatures of −20° C. to 100° C., preferably of −10° C. to 80° C., more preferably of 0° C. to 70° C. and especially preferably of 10° C. to 65° C.

In practice, the reaction is started by addition of a maximum of 10% of the total amount of the compound (III), and the compound (III) is then added as a 10%-90%, preferably 15%-75%, more preferably 20%-50%, solution in the solvent S1, in the course of which the temperature T varies within the range described above and the reaction can be kept under exothermic control by uniform addition of the compound (III). For start-up of the reaction, it is additionally optionally possible to use the compounds known to those skilled in the art such as dibromoethane or iodine, or else to activate the metal surface M by means of ultrasound.

It is advantageous to ensure good mixing of the mixture over the entire duration of the reaction, for example by stirring, and to enable good starting of the reaction through choice of a suitable solvent.

By means of the process according to the invention, distinctly better yields are obtained compared to the known processes, for example yields that are at least one-and-a-half times as high.

The invention likewise provides the triaryl organoborates preparable or prepared by the process according to the invention. The triaryl organoborates thus obtainable or obtained additionally preferably contain <10 000 ppm of a tetraarylborate $R_4^3B^-$, more preferably <5000 ppm of a tetraarylborate $R_4^3B^-$ and especially preferably <1000 ppm of a tetraarylborate $R_4^3B^-$. The unit ppm is based on parts by weight. The presence of tetraarylborates $R_4^3B^-$, in the case of prolonged storage, leads to limited writability of unexposed photopolymer films comprising the triaryl organoborates according to the invention or loss of the holographic properties in unexposed photopolymer films.

The invention further provides compounds of the formula (C), where the borate component can optionally be prepared or is prepared by the process according to the invention,

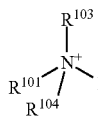 (C)

in which
$R^{101}$ is an optionally branched $C_{14}$- to $C_{22}$-alkyl radical or is additionally defined as $R^{102}$, with the proviso that $T^{101}$ and $R^{131}$ together and $T^{102}$ and $R^{132}$ together each contain at least 12 carbon atoms,
$R^{102}$ is a radical of the formulae

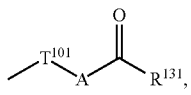 (CI)

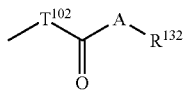 (CII)

$T^{101}$ is a bridge having 2 to 16 carbon atoms, of which not more than one third may be replaced by O and/or $NR^{200}$, where there must be at least 2 carbon atoms between O or $NR^{200}$, and which may be arranged in the form of an optionally branched chain and/or a five- or six-membered ring,
$R^{131}$ is an optionally branched and/or optionally substituted $C_4$- to $C_{22}$-alkyl radical, an optionally branched and/or optionally substituted $C_4$- to $C_{22}$-alkenyl radical, a cyclopentyl, cyclohexyl or cycloheptyl radical, a $C_7$- to $C_{10}$-aralkyl radical, a phenyl radical or heterocyclic radical optionally substituted by nonionic radicals, an optionally branched and/or optionally substituted $C_4$- to $C_{22}$-alkoxy radical, a cyclopentoxy, cyclohexoxy or cycloheptoxy radical, a $C_7$- to $C_{10}$-aralkoxy radical, a phenoxy radical or heteroaryloxy radical optionally substituted by nonionic radicals, an optionally branched and/or optionally substituted $C_4$- to $C_{22}$-alkylamino radical, a cyclopentylamino, cyclohexylamino or cycloheptylamino radical, a $C_7$- to $C_{10}$-aralkylamino radical, a phenylamino radical or heteroarylamino radical optionally substituted by nonionic radicals,
$T^{102}$ is a bridge having 1 to 16 carbon atoms which may be arranged in the form of an optionally branched chain and/or a five- or six-membered ring,
$R^{132}$ is an optionally branched and/or optionally substituted $C_1$- to $C_{22}$-alkyl radical, a cyclopentyl, cyclohexyl or cycloheptyl radical, a $C_7$- to $C_{10}$-aralkyl radical, a phenyl radical or heterocyclic radical optionally substituted by nonionic radicals,
A is $NR^{201}$ or oxygen,
$R^{200}$ and $R^{201}$ are independently hydrogen or $C_1$- to $C_4$-alkyl,
$R^{103}$ and $R^{104}$ are independently an optionally branched and/or optionally substituted $C_1$- to $C_5$-alkyl radical
or
$R^{102}$ is a radical of the formulae

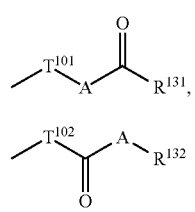 (CI)

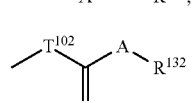 (CII)

$T^{101}$, $R^{131}$, $T^{102}$, $R^{132}$, $R^{200}$, $R^{201}$ and A have the definition given above, with the proviso that $T^{101}$ and $R^{131}$ together and $T^{102}$ and $R^{132}$ together each contain at least 12 carbon atoms,
$R^{101}$, $R^{103}$ and $R^{104}$ together with the $N^+$ atom form an imidazole or pyridine ring substituted at least by one radical selected from $C_1$- to $C_5$-alkyl, $C_1$- to $C_8$-alkoxy, $C_5$- to $C_7$-cycloalkyl, benzyl or phenyl
or
$R^{101}$ is an optionally branched $C_{14}$- to $C_{22}$-alkyl radical or is additionally defined as $R^{102}$, with the proviso that $T^{101}$ and $R^{131}$ together and $T^{102}$ and $R^{132}$ together each contain at least 12 carbon atoms,
$R^{102}$ is a radical of the formulae

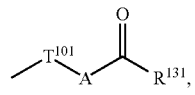 (CI)

-continued

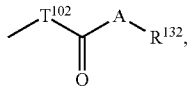
(CII)

and $T^{101}$, $R^{131}$, $T^{102}$, $R^{132}$, $R^{200}$, $R^{201}$ and A have the definition given above,
$R^{103}$ and $R^{104}$ together form a —(CH$_2$)$_4$—, —(CH$_2$)$_5$— or —(CH$_2$)$_2$—O—(CH$_2$)$_2$— bridge and
$R^1$ and $R^4$ are as defined above.

Preference is given to compounds of the formula (C)
in which
$R^{101}$ is an optionally branched $C_{14}$- to $C_{22}$-alkyl radical or is additionally defined as $R^{102}$, with the proviso that $T^{101}$ and $R^{131}$ together and $T^{102}$ and $R^{132}$ together each contain at least 12 carbon atoms,
$R^{102}$ is a radical of the formulae

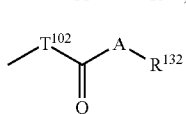
(CI)

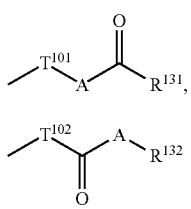
(CII)

$T^{101}$ is a bridge having 2 to 9 carbon atoms, of which not more than one third may be replaced by O and/or $NR^{200}$, where there must be at least 2 carbon atoms between O or $NR^{200}$, and which may be arranged in the form of an optionally branched chain and/or a five- or six-membered ring.
$R^{131}$ is an optionally branched and/or optionally substituted $C_4$- to $C_{16}$-alkyl radical, an optionally branched and/or optionally substituted $C_4$- to $C_{16}$-alkenyl radical, a cyclopentyl or cyclohexyl radical, a benzyl, phenethyl or phenylpropyl radical, a phenyl radical or heterocyclic radical optionally substituted by nonionic radicals, an optionally branched and/or optionally substituted $C_4$- to $C_{16}$-alkoxy radical, a cyclopentoxy or cyclohexoxy radical, a benzyloxy, phenethyloxy or phenylpropoxy radical, a phenoxy radical or heteroaryloxy radical optionally substituted by nonionic radicals, an optionally branched and/or optionally substituted $C_4$- to $C_{22}$-alkylamino radical, a cyclopentylamino or cyclohexylamino radical, a benzylamino, phenethylamino or phenylpropylamino radical, a phenylamino radical or heteroarylamino radical optionally substituted by nonionic radicals,
$T^{102}$ is a bridge having 1 to 9 carbon atoms which may be arranged in the form of an optionally branched chain and/or a five- or six-membered ring,
$R^{132}$ is an optionally branched and/or optionally substituted $C_1$- to $C_{16}$-alkyl radical, a cyclopentyl or cyclohexyl radical, a benzyl, phenethyl or phenylpropyl radical, a phenyl radical or heterocyclic radical optionally substituted by nonionic radicals,
A is $NR^{201}$ or oxygen,
$R^{200}$ and $R^{201}$ are independently hydrogen, methyl or ethyl,
$R^{103}$ and $R^{104}$ are independently an optionally branched and/or optionally substituted $C_1$- to $C_5$-alkyl radical or
$R^{102}$ is a radical of the formulae

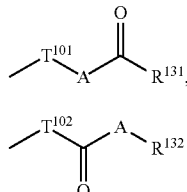
(CI)

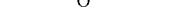
(CII)

$T^{101}$, $R^{131}$, $T^{102}$, $R^{132}$, $R^{200}$, $R^{201}$ and A have the definition given above, with the proviso that $T^{101}$ and $R^{131}$ together and $T^{102}$ and $R^{132}$ together each contain 12 carbon atoms,
$R^{101}$, $R^{103}$ and $R^{104}$ together with the $N^+$ atom form an imidazole or pyridine ring substituted at least by one radical selected from $C_1$- to $C_6$-alkyl, $C_1$- to $C_6$-alkoxy, cyclopentyl, cyclohexyl, benzyl or phenyl
or
$R^{101}$ is an optionally branched $C_{14}$- to $C_{22}$-alkyl radical or is additionally defined as $R^{102}$, with the proviso that $T^{101}$ and $R^{131}$ together and $T^{102}$ and $R^{132}$ together each contain at least 12 carbon atoms,
$R^{102}$ is a radical of the formulae

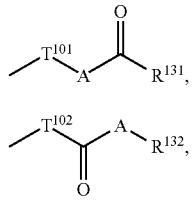
(CI)

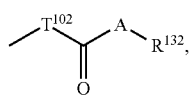
(CII)

and $T^{101}$, $R^{131}$, $T^{102}$, $R^{132}$, $R^{200}$, $R^{201}$ and A have the definition given above,
$R^{103}$ and $R^{104}$ together form a —(CH$_2$)$_4$—, —(CH$_2$)$_5$— or —(CH$_2$)$_2$—O—(CH$_2$)$_2$— bridge and
$R^1$ and $R^4$ are as defined above.

Particular preference is given to compounds of the formula (C)
in which
$R^{101}$ is an optionally branched $C_{14}$- to $C_{22}$-alkyl radical,
$R^{102}$ is a radical of the formulae

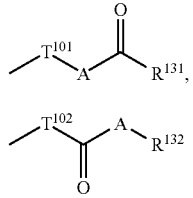
(CI)

(CII)

$T^{101}$ is a bridge in the form of an optionally branched chain which has 2 to 8 carbon atoms and may contain 1 or 2 oxygen atoms, where there must be at least 2 carbon atoms between two oxygen atoms, or a bridge of the formulae

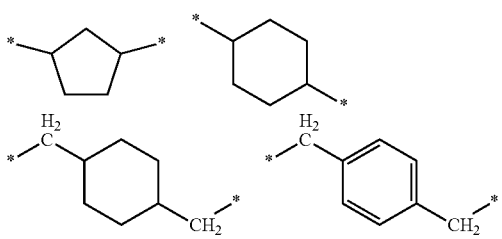

$R^{131}$ is an optionally branched and/or optionally substituted $C_4$- to $C_{16}$-alkyl radical, a cyclopentyl or cyclohexyl radical, a benzyl radical, a phenyl radical optionally substituted by nonionic radicals or a furyl, thienyl or pyridyl radical, an optionally branched and/or optionally substituted $C_4$- to $C_{16}$-alkoxy radical, a cyclopentoxy or cyclohexoxy radical, a benzyloxy radical, a phenoxy radical optionally substituted by nonionic radicals, an optionally branched and/or optionally substituted $C_4$- to $C_{22}$-alkylamino radical, a cyclopentylamino or cyclohexylamino radical, a benzylamino radical, a phenylamino radical or pyridylamino radical optionally substituted by nonionic radicals, $T^{102}$ is a bridge in the form of an optionally branched chain having 2 to 8 carbon atoms or is a bridge of the formulae

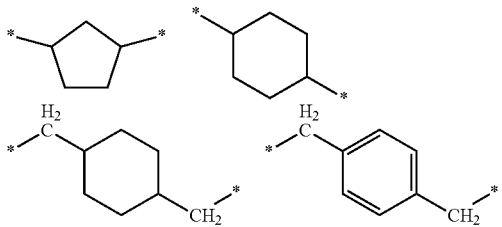

$R^{132}$ is an optionally branched and/or optionally substituted $C_1$- to $C_{16}$-alkyl radical, a cyclopentyl or cyclohexyl radical, a benzyl radical, a phenyl radical or pyridyl radical optionally substituted by nonionic radicals, A is $NR^{201}$ or oxygen, $R^{201}$ is hydrogen or methyl, $R^{103}$ and $R^{104}$ are independently an optionally branched and/or optionally substituted $C_1$- to $C_5$-alkyl radical or $R^{102}$ is a radical of the formulae

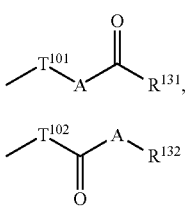

$T^{101}$, $R^{131}$, $T^{102}$, $R^{132}$, $R^{201}$ and A have the definition given above, with the proviso that $T^{101}$ and $R^{131}$ together and $T^{102}$ and $R^{132}$ together each contain 12 carbon atoms, $R^{101}$, $R^{103}$ and $R^{104}$ together with the $N^+$ atom form an imidazole or pyridine ring substituted at least by one radical selected from $C_1$- to $C_4$-alkyl, $C_1$- to $C_4$-alkoxy, cyclopentyl, cyclohexyl, benzyl or phenyl or $R^{101}$ is an optionally branched $C_{14}$- to $C_{22}$-alkyl radical, $R^{102}$ is a radical of the formulae

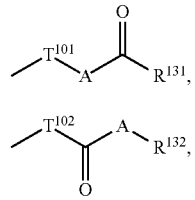

and $T^{101}$, $R^{131}$, $T^{102}$, $R^{132}$, $R^{201}$ and A have the definition given above, $R^{103}$ and $R^{104}$ together form a $-(CH_2)_4-$, $-(CH_2)_5-$ or $-(CH_2)_2-O-(CH_2)_2-$ bridge and $R^1$ and $R^4$ are as defined above.

$R^{131}$ and $R^{132}$ are also understood to mean those radicals that are attached via two or more bonds to the groups of the formulae

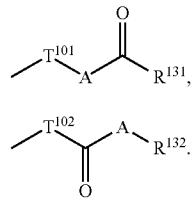

Examples of such bi- or oligofunctional $R^{131}$ are $-(CH_2)_4-$, $-NH-(CH_2)_6-NH-$,

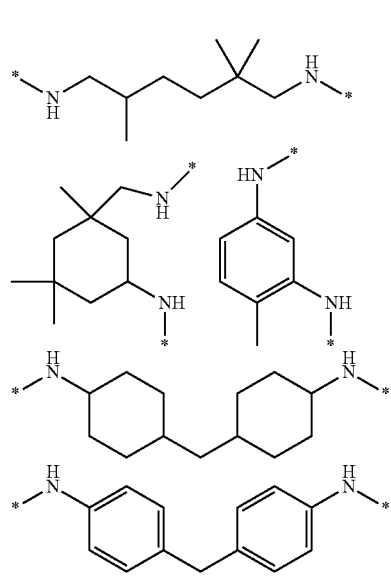

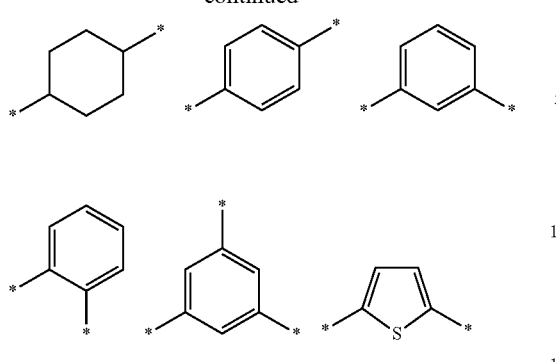

Examples of such bi- or oligofunctional $R^{132}$ are —$(CH_2)_2$—, —$(CH_2)_4$—, —$(CH_2)_2$—O—$(CH_2)_2$—,

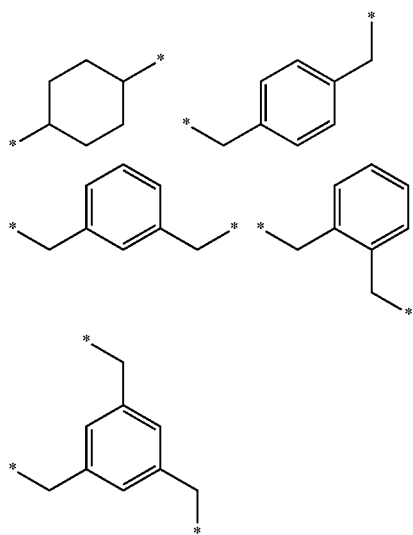

Examples of bridges $T^{101}$ are —$(CH_2)_2$—, —$(CH_2)_3$—, —$(CH_2)_4$—, —$CH_2CH(CH_3)$—, —$(CH_2)_2$—O—$(CH_2)_2$—, —[$(CH_2)_2$—O-]$_2(CH_2)_2$—, —$(CH_2)_4$—O—$CH_2$—$CH_2$—,

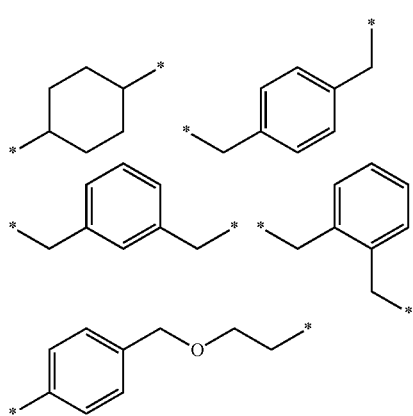

Examples of bridges $T^{102}$ are —$CH_2$—, —$(CH_2)_2$—, —$(CH_2)_3$—, —$(CH_2)_4$—, —$CH_2CH(CH_3)$—, —$(CH_2)_5$—, —$(CH_2)_6$—,

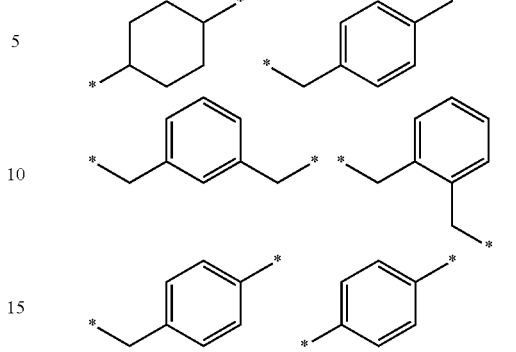

A heterocyclic radical should be understood to mean a five- or six-membered aromatic or quasi-aromatic, partly saturated or saturated ring which optionally contains at least one N, O or S and is optionally benzofused and/or substituted by nonionic radicals. The same is meant by the heterocyclic radical in heteroaryloxy and heteroarylamino.

Examples are: pyridyl, benzothiazolyl, thienyl, piperidyl.

A nonionic radical is understood to mean: halogen, alkyl, alkoxy, cyano, nitro, COO-alkyl.

Examples of halogen, alkyl, alkoxy are fluorine, chlorine, bromine, methyl, ethyl, methoxy.

The invention further provides compounds of the formula (CC), where the borate component can optionally be prepared or is prepared by the process according to the invention, $$(R^4)_{\overline{3}}—B^-—R^1 \quad \begin{matrix} R^{303} & & R^{303'} \\ \diagdown & & \diagup \\ N^+—R^{302}—N^+ \\ \diagup & & \diagdown \\ R^{301} & & R^{301'} \\ R^{304} & & R^{304'} \end{matrix} \quad (R^4)_{\overline{3}}—B^-—R^1$$ (CC)

in which $R^{301}$ and $R^{301'}$ are each independently an optionally branched $C_{14}$- to $C_{22}$-alkyl radical or are additionally defined as $R^{302}$, with the proviso that $T^{301}$ and $R^{331}$ together and $T^{302}$ and $R^{332}$ together each contain at least 12 carbon atoms, $R^{302}$ is a radical of the formulae $$\diagup T^{301}\diagdown_A \overset{O}{\underset{\|}{C}}\diagup R^{331}\diagdown \overset{O}{\underset{\|}{C}}\diagup_A T^{301}\diagdown,$$ (CCI)

$$\diagup T^{302}\diagdown_A \overset{}{\underset{\underset{O}{\|}}{C}}\diagup R^{332}\diagdown \overset{}{\underset{\underset{O}{\|}}{C}}\diagup_A T^{302}\diagdown,$$ (CCII)

$T^{301}$ is a bridge having 2 to 16 carbon atoms, of which not more than one third may be replaced by O and/or $NR^{400}$, where there must be at least 2 carbon atoms between O or $NR^{200}$, and which may be arranged in the form of an optionally branched chain and/or a five- or six-membered ring, $R^{331}$ is an optionally branched and/or optionally substituted $C_4$- to $C_{22}$-alkylene radical, a cyclopentylene, cyclohexylene or cycloheptylene radical, a $C_8$- to $C_{12}$-aryldialkylene radical, an arylene radical or heteroarylene radical optionally substituted by nonionic radicals, an optionally branched and/or optionally substituted $C_4$- to $C_{22}$-alkanedioxy radical, a cyclopentanedioxy, cyclohexanedioxy or cycloheptanedioxy radical, a $C_7$- to $C_{12}$-oxyarylalkyloxy radical, a $C_8$- to $C_{12}$-aryldi(alkyloxy) radical, a benzenedioxy radical or heteroaryldioxy radical optionally substituted by nonionic radicals, an optionally branched and/or optionally substituted $C_4$- to $C_{22}$-alkanediamino radical, a cyclopentanediamino, cyclohexanediamino or cycloheptanediamino radical, a $C_8$- to $C_{12}$-aminoarylalkylamino radical, a benzenediamino radical or heteroarylenediamino radical optionally substituted by nonionic radicals, an alkylene-cycloalkylene radical, alkanedicycloalkylene radical or alkanediarylene radical, $T^{302}$ is a bridge having 1 to 16 carbon atoms which may be arranged in the form of an optionally branched chain and/or a five- or six-membered ring, $R^{332}$ is an optionally branched and/or optionally substituted $C_1$- to $C_{22}$-alkylene radical, a cyclopentylene, cyclohexylene or cycloheptylene radical, a $C_8$- to $C_{12}$-aralkylene radical, an arylene or heteroarylene radical optionally substituted by nonionic radicals, A is $NR^{401}$ or oxygen, $R^{400}$ and $R^{401}$ are independently hydrogen or $C_1$- to $C_4$-alkyl, $R^{303}$, $R^{304}$, $R^{303'}$ and $R^{304'}$ are independently an optionally branched and/or optionally substituted $C_1$- to $C_5$-alkyl radical, or $R^{302}$ is a radical of the formulae

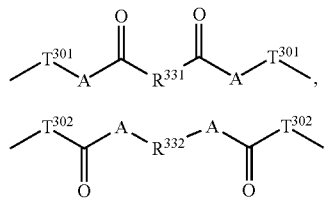

(CCI)

(CCII)

$T^{301}$, $R^{331}$, $T^{302}$, $R^{332}$, $R^{400}$, $R^{401}$ and A have the definition given above, with the proviso that $T^{301}$ and $R^{331}$ together and $T^{302}$ and $R^{332}$ together each contain at least 12 carbon atoms, $R^{301}$, $R^{303}$ and $R^{304}$ together with the $N^+$ atom form an imidazole or pyridine ring substituted at least by one radical selected from $C_1$- to $C_8$-alkyl, $C_1$- to $C_8$-alkoxy, $C_5$- to $C_7$-cycloalkyl, benzyl or phenyl, and/or $R^{301'}$, $R^{303'}$ and $R^{304'}$ together with the $N^+$ atom form an imidazole or pyridine ring substituted at least by one radical selected from $C_1$- to $C_8$-alkyl, $C_1$- to $C_8$-alkoxy, $C_5$- to $C_7$-cycloalkyl, benzyl or phenyl, or $R^{301}$ and $R^{301'}$ are each independently an optionally branched $C_{14}$- to $C_{22}$-alkyl radical or are additionally defined as $R^{302}$, with the proviso that $T^{301}$ and $R^{331}$ together and $T^{302}$ and $R^{332}$ together each contain at least 12 carbon atoms, $R^{302}$ is a radical of the formulae

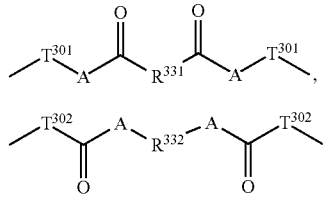

(CCI)

(CCII)

and
$T^{301}$, $R^{331}$, $T^{302}$, $R^{332}$, $R^{400}$, $R^{401}$ and A have the definition given above, $R^{303}$ and $R^{304}$ together form a $-(CH_2)_4-$, $-(CH_2)_5-$ or $-(CH_2)_2-O-(CH_2)_2-$ bridge, and/or $R^{303'}$ and $R^{304'}$ together form a $-(CH_2)_4-$, $-(CH_2)_5-$ or $-(CH_2)_2-O-(CH_2)_2-$ bridge, and $R^1$ and $R^4$ are as defined above.

Preference is given to compounds of the formula (CC) in which $R^{301}$ and $R^{301'}$ are each independently an optionally branched $C_{14}$- to $C_{22}$-alkyl radical or are additionally defined as $R^{302}$, with the proviso that $T^{301}$ and $R^{331}$ together and $T^{302}$ and $R^{332}$ together each contain at least 12 carbon atoms, $R^{302}$ is a radical of the formulae

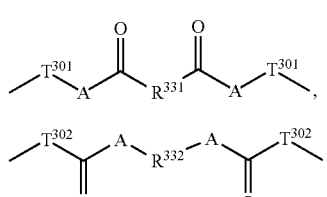

(CCI)

(CCII)

$T^{301}$ is a bridge having 2 to 9 carbon atoms, of which not more than one third may be replaced by O and/or $NR^{400}$, where there must be at least 2 carbon atoms between two O or $NR^{400}$, and which may be arranged in the form of an optionally branched chain and/or a five- or six-membered ring, $R^{331}$ is an optionally branched and/or optionally substituted $C_4$- to $C_{16}$-alkylene radical, a cyclopentylene or cyclohexylene radical, a xylylene, benzenediethylene or benzenedipropylene radical, an arylene radical or heteroarylene radical optionally substituted by nonionic radicals, an optionally branched and/or optionally substituted $C_4$- to $C_{16}$-alkanedioxy radical, a cyclopentanedioxy or cyclohexanedioxy radical, a benzenedi(methyloxy), benzenedi(ethyloxy) or benzenedi(propyloxy) radical, a benzenedioxy radical or heteroarylenedioxy radical optionally substituted by nonionic radicals, an optionally branched and/or optionally substituted $C_4$- to $C_{22}$-alkanediamino radical, a cyclopentanediamino or cyclohexanediamino radical, a benzenedi(methylamino), benzenedi(ethylamino) or benzenedi(propylamino) radical, a benzenediamino radical, methyldicyclohexylene radical, 4-methylenebis(4,1-phenylene) radical or heteroarylenediamino radical optionally substituted by nonionic radicals, $T^{302}$ is a bridge having 1 to 9 carbon atoms which may be arranged in the form of an optionally branched chain and/or a five- or six-membered ring.

$R^{332}$ is an optionally branched and/or optionally substituted $C_1$- to $C_{16}$-alkylene radical, a cyclopentylene or cyclohexylene radical, xylylene, benzenediethylene or benzenedipropylene radical, an arylene or heteroarylene radical optionally substituted by nonionic radicals,
A is $NR^{401}$ or oxygen,
$R^{400}$ and $R^{401}$ are independently hydrogen, methyl or ethyl,
$R^{303}$ and $R^{304}$ are independently an optionally branched and/or optionally substituted $C_1$- to $C_5$-alkyl radical, and/or
$R^{303'}$ and $R^{304'}$ are independently an optionally branched and/or optionally substituted $C_1$- to $C_5$-alkyl radical,
or
$R^{302}$ is a radical of the formulae

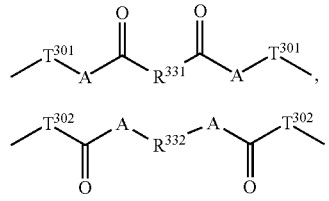

(CCI)

(CCII)

$T^{301}$, $R^{331}$, $T^{302}$, $R^{332}$, $R^{400}$, $R^{401}$ and A have the definition given above, with the proviso that $T^{301}$ and $R^{331}$ together and $T^{302}$ and $R^{332}$ together each contain 12 carbon atoms,
$R^{301}$, $R^{303}$ and $R^{304}$ together with the N$^+$ atom form an imidazole or pyridine ring substituted at least by one radical selected from $C_1$- to $C_6$-alkyl, $C_1$- to $C_6$-alkoxy, cyclopentyl, cyclohexyl, benzyl or phenyl, and/or
$R^{301'}$, $R^{303'}$ and $R^{304'}$ together with the N$^+$ atom form an imidazole or pyridine ring substituted at least by one radical selected from $C_1$- to $C_6$-alkyl, $C_1$- to $C_6$-alkoxy, cyclopentyl, cyclohexyl, benzyl or phenyl,
or
$R^{301}$ and $R^{301'}$ are each independently an optionally branched $C_{14}$- to $C_{22}$-alkyl radical or are additionally defined as $R^{302}$, with the proviso that $T^{301}$ and $R^{331}$ together and $T^{302}$ and $R^{332}$ together each contain at least 12 carbon atoms,
$R^{302}$ is a radical of the formulae

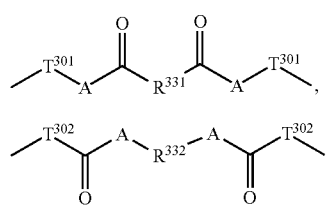

(CCI)

(CCII)

and
$T^{301}$, $R^{331}$, $T^{302}$, $R^{332}$, $R^{400}$, $R^{401}$ and A have the definition given above,
$R^{303}$ and $R^{304}$ together form a —(CH$_2$)$_4$—, —(CH$_2$)$_5$— or —(CH$_2$)$_2$—O—(CH$_2$)$_2$— bridge, and/or
$R^{303'}$ and $R^{304'}$ together form a —(CH$_2$)$_4$—, —(CH$_2$)$_5$— or —(CH$_2$)$_2$—O—(CH$_2$)$_2$— bridge
and
$R^1$ and $R^4$ are as defined above.

Particular preference is given to compounds of the formula (CC)

in which
$R^{301}$ and $R^{301'}$ are each independently an optionally branched $C_{14}$- to $C_{22}$-alkyl radical,
$R^{302}$ is a radical of the formulae

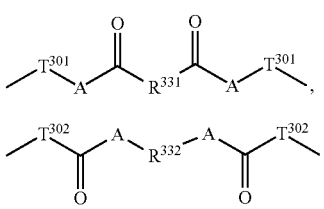

(CCI)

(CCII)

$T^{301}$ is a bridge in the form of an optionally branched chain which has 2 to 8 carbon atoms and may contain 1 or 2 oxygen atoms, where there must be at least 2 carbon atoms between two oxygen atoms, or a bridge of the formulae

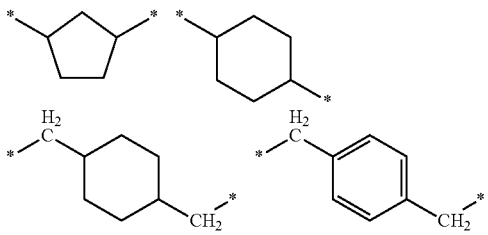

$R^{331}$ is an optionally branched and/or optionally substituted $C_4$- to $C_{16}$-alkylene radical, a cyclopentylene or cyclohexylene radical, a xylylene radical, an arylene radical optionally substituted by nonionic radicals or a furylene, thienylene or pyridylene radical, an optionally branched and/or optionally substituted $C_4$- to $C_{16}$-alkanedioxy radical, a cyclopentanedioxy or cyclohexanedioxy radical, a benzenedi(methyloxy) radical, a benzenedioxy radical optionally substituted by nonionic radicals, an optionally branched and/or optionally substituted $C_4$- to $C_{22}$-alkanediamino radical, a cyclopentanediamino or cyclohexanediamino radical, a benzenedi(methylamino) radical, a benzenediamino radical or pyridinediamino radical optionally substituted by nonionic radicals,
$T^{302}$ is a bridge in the form of an optionally branched chain having 2 to 8 carbon atoms or is a bridge of the formulae

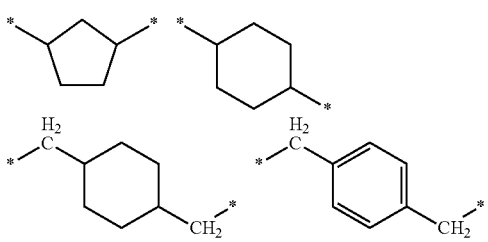

$R^{332}$ is an optionally branched and/or optionally substituted $C_1$- to $C_{16}$-alkylene radical, a cyclopentylene or cyclohexylene radical, a xylylene radical, an arylene radical or pyridylene radical optionally substituted by nonionic radicals,
A is $NR^{401}$ or oxygen,
$R^{401}$ is hydrogen or methyl, $R^{303}$ and $R^{304}$ are independently an optionally branched and/or optionally substituted $C_1$- to $C_5$-alkyl radical, and/or
$R^{303'}$ and $R^{304'}$ are independently an optionally branched and/or optionally substituted $C_1$- to $C_5$-alkyl radical
or
$R^{302}$ is a radical of the formulae

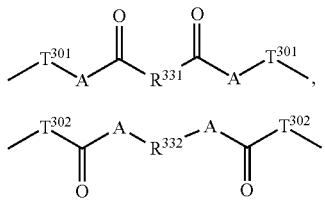
(CCI)

(CCII)

$T^{301}$, $R^{331}$, $T^{302}$, $R^{332}$, $R^{400}$, $R^{401}$ and A have the definition given above, with the proviso that $T^{301}$ and $R^{331}$ together and $T^{302}$ and $R^{332}$ together each contain at least 12 carbon atoms,
$R^{301}$, $R^{303}$ and $R^{304}$ together with the $N^+$ atom form an imidazole or pyridine ring substituted at least by one radical selected from $C_1$- to $C_4$-alkyl, $C_1$- to $C_4$-alkoxy, cyclopentyl, cyclohexyl, benzyl or phenyl, and/or
$R^{301'}$, $R^{303'}$, and $R^{304'}$ together with the $N^+$ atom form an imidazole or pyridine ring substituted at least by one radical selected from $C_1$- to $C_4$-alkyl, $C_1$- to $C_4$-alkoxy, cyclopentyl, cyclohexyl, benzyl or phenyl
or
$R^{301}$ and $R^{301'}$ are each independently an optionally branched $C_{14}$- to $C_{22}$-alkyl radical,
$R^{302}$ is a radical of the formulae

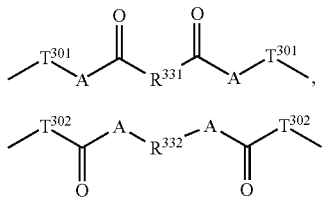
(CCI)

(CCII)

and
$T^{301}$, $R^{331}$, $T^{302}$, $R^{332}$, $R^{400}$, $R^{401}$ and A have the definition given above,
$R^{303}$ and $R^{304}$ together form a $—(CH_2)_4—$, $—(CH_2)_5—$ or $—(CH_2)_2—O—(CH_2)_2—$ bridge, and/or
$R^{303'}$ and $R^{304'}$ together form a $—(CH_2)_4—$, $—(CH_2)_5—$ or $—(CH_2)_2—O—(CH_2)_2—$ bridge
and
$R^1$ and $R^4$ are as defined above.

Very particular preference is given to compounds of the formula (CC)
in which
$R^{301}$ and $R^{301'}$, $R^{302}$ and $R^{302'}$, and $R^{303}$ and $R^{303'}$ as pairs are the same, and the other radicals have the definitions given above.

$R^{331}$ and $R^{332}$ in the formulae

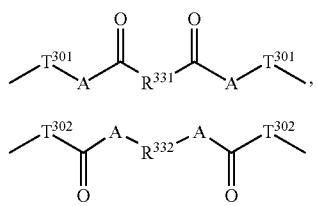
(CCI)

(CCII)

are also understood to mean those radicals that are attached via three or more bonds to the groups of the formulae

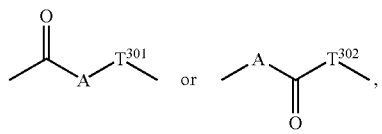

Examples of such bi- or oligofunctional $R^{331}$ are $—(CH_2)_4—$, $—NH—(CH_2)_6—NH—$,

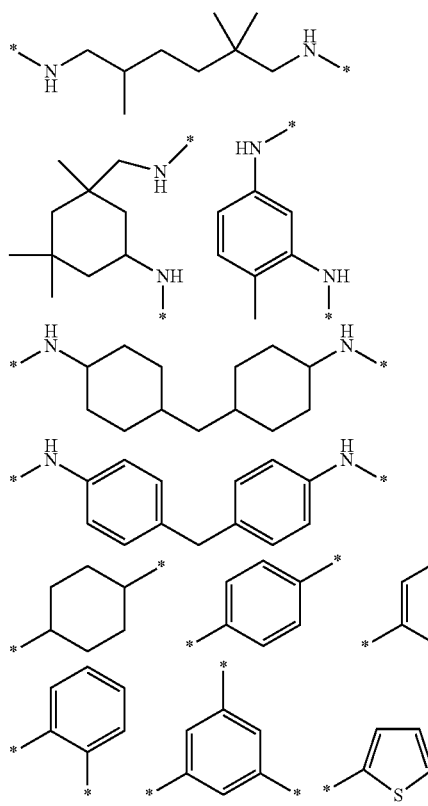

Examples of such bi- or oligofunctional $R^{332}$ are $—(CH_2)_2—$, $—(CH_2)_4—$, $—(CH_2)_2—O—(CH_2)_2—$,

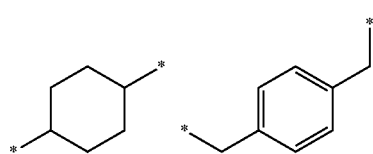

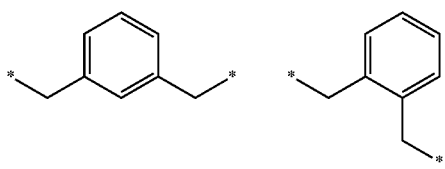

Examples of bridges $T^{301}$ are —(CH$_2$)$_2$—, —(CH$_2$)$_3$—, —(CH$_2$)$_4$—, —CH$_2$CH(CH$_3$)—, —(CH$_2$)$_2$—O—(CH$_2$)$_2$—, —[(CH$_2$)$_2$—O-]$_2$(CH$_2$)$_2$—, —(CH$_2$)$_4$—O—CH$_2$—CH$_2$—,

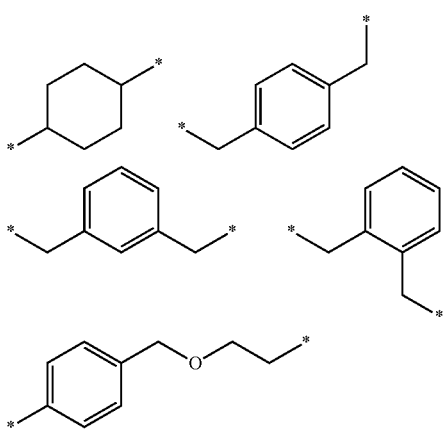

Examples of bridges $T^{302}$ are —CH$_2$—, —(CH$_2$)$_2$—, —(CH$_2$)$_3$—, —(CH$_2$)$_4$—, —CH$_2$CH(CH$_3$)—, —(CH$_2$)$_5$—, —(CH$_2$)$_6$—,

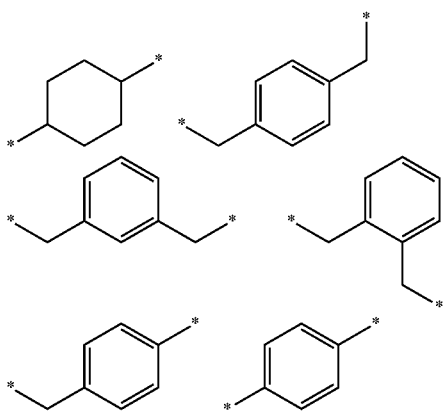

A heterocyclic radical should be understood to mean a five- or six-membered aromatic or quasi-aromatic, partly saturated or saturated ring which optionally contains at least one N, O or S and is optionally benzofused and/or substituted by nonionic radicals. The same is meant by the heterocyclic radical in heteroaryloxy and heteroarylamino.

Examples are: pyridyl, benzothiazolyl, thienyl, piperidyl.

A nonionic radical is understood to mean: halogen, alkyl, alkoxy, cyano, nitro, COO-alkyl.

Examples of halogen, alkyl, alkoxy are fluorine, chlorine, bromine, methyl, ethyl, methoxy.

The matrix polymers of the photopolymer formulation according to the invention may especially be in a crosslinked state and more preferably in a three-dimensionally crosslinked state.

The invention likewise provides the triaryl organoborates preparable or prepared by the process according to the invention.

The invention further provides for the use of the triaryl organoborates preparable or prepared in accordance with the invention or of the above-described compounds of the formula (C) or of the above-described compounds of the formula (CC) in photoinitiator systems, and also photopolymer compositions comprising a photopolymerizable component and a photoinitiator system comprising the triaryl organoborates prepared in accordance with the invention. In addition, holographic media and holograms obtainable therefrom are accessible from the photopolymer compositions mentioned.

Suitable matrix polymers of a corresponding photopolymer formulation may especially be in a crosslinked state and more preferably in a three-dimensionally crosslinked state.

It is also advantageous for the matrix polymers to be polyurethanes, in which case the polyurethanes may be obtainable in particular by reacting at least one polyisocyanate component a) with at least one isocyanate-reactive component b).

The polyisocyanate component a) preferably comprises at least one organic compound having at least two NCO groups. These organic compounds may especially be monomeric di- and triisocyanates, polyisocyanates and/or NCO-functional prepolymers. The polyisocyanate component a) may also contain or consist of mixtures of monomeric di- and triisocyanates, polyisocyanates and/or NCO-functional prepolymers.

Monomeric di- and triisocyanates used may be any of the compounds that are well known to the person skilled in the art or mixtures thereof. These compounds may have aromatic, araliphatic, aliphatic or cycloaliphatic structures. In minor amounts, the monomeric di- and triisocyanates may also comprise monoisocyanates, i.e. organic compounds having one NCO group.

Examples of suitable monomeric di- and triisocyanates are butane 1,4-diisocyanate, pentane 1,5-diisocyanate, hexane 1,6-diisocyanate (hexamethylene diisocyanate, HDI), 2,2,4-trimethylhexamethylene diisocyanate and/or 2,4,4-trimethylhexamethylene diisocyanate (TMDI), isophorone diisocyanate (IPDI), 1,8-diisocyanato-4-(isocyanatomethyl)octane, bis(4,4'-isocyanatocyclohexyl)methane and/or bis(2',4-isocyanatocyclohexyl)methane and/or mixtures thereof with any isomer content, cyclohexane 1,4-diisocyanate, the isomeric bis(isocyanatomethyl)cyclohexanes, 2,4- and/or 2,6-diisocyanato-1-methylcyclohexane (hexahydrotolylene 2,4- and/or 2,6-diisocyanate, H$_6$-TDI), phenylene 1,4-diisocyanate, tolylene 2,4- and/or 2,6-diisocyanate (TDI), naphthylene 1,5-diisocyanate (NDI), diphenylmethane 2,4'- and/or 4,4'-diisocyanate (MDI), 1,3-bis(isocyanatomethyl)benzene (XDI) and/or the analogous 1,4 isomer, or any desired mixtures of the aforementioned compounds.

Suitable polyisocyanates are compounds which have urethane, urea, carbodiimide, acylurea, amide, isocyanurate, allophanate, biuret, oxadiazinetrione, uretdione and/or iminooxadiazinedione structures and are obtainable from the aforementioned di- or triisocyanates.

More preferably, the polyisocyanates are oligomerized aliphatic and/or cycloaliphatic di- or triisocyanates, and it is especially possible to use the above aliphatic and/or cycloaliphatic di- or triisocyanates.

Very particular preference is given to polyisocyanates having isocyanurate, uretdione and/or iminooxadiazinedione structures and to biurets based on HDI or mixtures thereof.

Suitable prepolymers contain urethane and/or urea groups, and optionally further structures formed through modification of NCO groups as specified above. Prepolymers of this kind are obtainable, for example, by reaction of the abovementioned monomeric di- and triisocyanates and/or polyisocyanates a1) with isocyanate-reactive compounds b1).

Isocyanate-reactive compounds b1) used may be alcohols or amino or mercapto compounds, preferably alcohols. These may especially be polyols. Most preferably, the isocyanate-reactive compound b1) used may be polyester polyols, polyether polyols, polycarbonate polyols, poly(meth)acrylate polyols and/or polyurethane polyols.

Suitable polyester polyols are, for example, linear polyester diols or branched polyester polyols which can be obtained in a known manner by reacting aliphatic, cycloaliphatic or aromatic di- or polycarboxylic acids or the anhydrides thereof with polyhydric alcohols of OH functionality ≥2. Examples of suitable di- or polycarboxylic acids are polybasic carboxylic acids such as succinic acid, adipic acid, suberic acid, sebacic acid, decanedicarboxylic acid, phthalic acid, terephthalic acid, isophthalic acid, tetrahydrophthalic acid or trimellitic acid, and acid anhydrides such as phthalic anhydride, trimellitic anhydride or succinic anhydride, or any desired mixtures thereof. The polyester polyols may also be based on natural raw materials such as castor oil. It is likewise possible that the polyester polyols are based on homo- or copolymers of lactones, which can preferably be obtained by adding lactones or lactone mixtures such as butyrolactone, ε-caprolactone and/or methyl-ε-caprolactone onto hydroxy-functional compounds such as polyhydric alcohols of OH functionality ≥2, for example of the kind specified below.

Examples of suitable alcohols are all polyhydric alcohols, for example the $C_2$-$C_{12}$ diols, the isomeric cyclohexanediols, glycerol or any desired mixtures with one another.

Suitable polycarbonate polyols are obtainable in a manner known per se by reacting organic carbonates or phosgene with diols or diol mixtures.

Suitable organic carbonates are dimethyl carbonate, diethyl carbonate and diphenyl carbonate.

Suitable diols or mixtures comprise the polyhydric alcohols of OH functionality ≥2 mentioned in the context of the polyester segments, preferably butane-1,4-diol, hexane-1,6-diol and/or 3-methylpentanediol. It is also possible to transform polyester polyols to polycarbonate polyols.

Suitable polyether polyols are polyaddition products, optionally of blockwise construction, of cyclic ethers onto OH- or NH-functional starter molecules.

Suitable cyclic ethers are, for example, styrene oxides, ethylene oxide, propylene oxide, tetrahydrofuran, butylene oxide, epichlorohydrin and any desired mixtures thereof.

Starters used may be the polyhydric alcohols of OH functionality ≥2 mentioned in the context of the polyester polyols, and also primary or secondary amines and amino alcohols.

Preferred polyether polyols are those of the aforementioned type based exclusively on propylene oxide, or random or block copolymers based on propylene oxide with further 1-alkylene oxides. Particular preference is given to propylene oxide homopolymers and random or block copolymers having oxyethylene, oxypropylene and/or oxybutylene units, where the proportion of the oxypropylene units based on the total amount of all oxyethylene, oxypropylene and oxybutylene units makes up at least 20% by weight, preferably at least 45% by weight. Oxypropylene and oxybutylene here include all respective linear and branched $C_3$ and $C_4$ isomers.

In addition, suitable constituents of the polyol component b1), as polyfunctional isocyanate-reactive compounds, are also aliphatic, araliphatic or cycloaliphatic di-, tri- or polyfunctional alcohols of low molecular weight, i.e. having molecular weights of 500 g/mol, and having short chains, i.e. containing 2 to 20 carbon atoms.

These may be, for example, in addition to the abovementioned compounds, neopentyl glycol, 2-ethyl-2-butylpropanediol, trimethylpentanediol, positionally isomeric diethyloctanediols, cyclohexanediol, cyclohexane-1,4-dimethanol, hexane-1,6-diol, cyclohexane-1,2- and -1,4-diol, hydrogenated bisphenol A, 2,2-bis(4-hydroxycyclohexyl)propane or 2,2-dimethyl-3-hydroxypropionic acid, 2,2-dimethyl-3-hydroxypropyl esters. Examples of suitable triols are trimethylolethane, trimethylolpropane or glycerol. Suitable higher-functionality alcohols are di(trimethylolpropane), pentaerythritol, dipentaerythritol or sorbitol.

It is particularly preferred when the polyol component is a difunctional polyether or polyester or a polyether-polyester block copolyester or a polyether-polyester block copolymer with primary OH functions.

It is likewise possible to use amines as isocyanate-reactive compounds b1). Examples of suitable amines are ethylenediamine, propylenediamine, diaminocyclohexane, 4,4'-dicyclohexylmethanediamine, isophoronediamine (IPDA), difunctional polyamines, for example the Jeffamines®, amine-terminated polymers, especially having number-average molar masses ≤10 000 g/mol. Mixtures of the aforementioned amines may likewise be used.

It is likewise possible to use amino alcohols as isocyanate-reactive compounds b1). Examples of suitable amino alcohols are the isomeric aminoethanols, the isomeric aminopropanols, the isomeric aminobutanols and the isomeric aminohexanols or any desired mixtures thereof.

All the aforementioned isocyanate-reactive compounds b1) can be mixed with one another as desired.

It is also preferable when the isocyanate-reactive compounds b1) have a number-average molar mass of ≥200 and ≤10 000 g/mol, further preferably ≥500 and ≤8000 g/mol and most preferably ≥800 and ≤5000 g/mol. The OH functionality of the polyols is preferably 1.5 to 6.0, more preferably 1.8 to 4.0.

The prepolymers of the polyisocyanate component a) may especially have a residual content of free monomeric di- and triisocyanates of <1% by weight, more preferably <0.5% by weight and most preferably <0.3% by weight.

It may also be possible for the polyisocyanate component a) to contain, in full or in part, an organic compound wherein the NCO groups have been wholly or partly reacted with blocking agents known from coating technology. Examples of blocking agents are alcohols, lactams, oximes, malonic esters, pyrazoles and amines, for example butanone oxime, diisopropylamine, diethyl malonate, ethyl acetoacetate, 3,5-dimethylpyrazole, ε-caprolactam or mixtures thereof.

It is particularly preferable when the polyisocyanate component a) comprises compounds having aliphatically bonded NCO groups, where aliphatically bonded NCO groups are understood to mean those groups bonded to a primary carbon atom. The isocyanate-reactive component b) preferably comprises at least one organic compound having an average of at least 1.5 and preferably 2 to 3 isocyanate-reactive groups. In the context of the present invention, isocyanate-reactive groups are preferably considered to be hydroxyl, amino or mercapto groups.

The isocyanate-reactive component may especially comprise compounds having a numerical average of at least 1.5 and preferably 2 to 3 isocyanate-reactive groups.

Suitable polyfunctional isocyanate-reactive compounds of component b) are, for example, the above-described compounds b1).

In a further preferred embodiment, the writing monomer c) comprises or consists of at least one monofunctional and/or one multifunctional writing monomer. Further preferably, the writing monomer may comprise or consist of at least one monofunctional and/or one multifunctional (meth)acrylate writing monomer. Most preferably, the writing monomer may comprise or consist of at least one monofunctional and/or one multifunctional urethane (meth)acrylate.

Suitable acrylate writing monomers are especially compounds of the general formula (V)

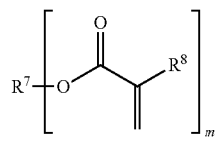

in which $m \geq 1$ and $m \leq 4$ and $R^7$ is a linear, branched, cyclic or heterocyclic organic moiety which is unsubstituted or else optionally substituted by heteroatoms and/or $R^8$ is hydrogen or a linear, branched, cyclic or heterocyclic organic moiety which is unsubstituted or else optionally substituted by heteroatoms. More preferably, $R^8$ is hydrogen or methyl and/or $R^7$ is a linear, branched, cyclic or heterocyclic organic moiety which is unsubstituted or else optionally substituted by heteroatoms.

Acrylates and methacrylates refer in the present context, respectively, to esters of acrylic acid and methacrylic acid. Examples of preferably usable acrylates and methacrylates are phenyl acrylate, phenyl methacrylate, phenoxyethyl acrylate, phenoxyethyl methacrylate, phenoxyethoxyethyl acrylate, phenoxyethoxyethyl methacrylate, phenylthioethyl acrylate, phenylthioethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, bisphenol A diacrylate, bisphenol A dimethacrylate, and their ethoxylated analogue compounds or N-carbazolyl acrylates.

Urethane acrylates are understood in the present context to mean compounds having at least one acrylic ester group and at least one urethane bond. Such compounds can be obtained, for example, by reacting a hydroxy-functional acrylate or methacrylate with an isocyanate-functional compound.

Examples of isocyanate-functional compounds usable for this purpose are monoisocyanates, and the monomeric diisocyanates, triisocyanates and/or polyisocyanates mentioned under a). Examples of suitable monoisocyanates are phenyl isocyanate, the isomeric methylthiophenyl isocyanates. Di-, tri- or polyisocyanates are mentioned above, and also triphenylmethane 4,4',4"-triisocyanate and tris(p-isocyanatophenyl) thiophosphate or derivatives thereof having urethane, urea, carbodiimide, acylurea, isocyanurate, allophanate, biuret, oxadiazinetrione, uretdione, iminooxadiazinedione structure and mixtures thereof. Preference is given here to aromatic di-, tri- or polyisocyanates.

Useful hydroxy-functional acrylates or methacrylates for the preparation of urethane acrylates include, for example, compounds such as 2-hydroxyethyl (meth)acrylate, polyethylene oxide mono(meth)acrylates, polypropylene oxide mono(meth)acrylates, polyalkylene oxide mono(meth)acrylates, poly(ε-caprolactone) mono(meth)acrylates, for example Tone® M100 (Dow, Schwalbach, Del.), 2-hydroxypropyl (meth)acrylate, 4-hydroxybutyl (meth)acrylate, 3-hydroxy-2,2-dimethylpropyl (meth)acrylate, hydroxypropyl (meth)acrylate, 2-hydroxy-3-phenoxypropyl acrylate, the hydroxy-functional mono-, di- or tetraacrylates of polyhydric alcohols such as trimethylolpropane, glycerol, pentaerythritol, dipentaerythritol, ethoxylated, propoxylated or alkoxylated trimethylolpropane, glycerol, pentaerythritol, dipentaerythritol or the technical grade mixtures thereof. Preference is given to 2-hydroxyethyl acrylate, hydroxypropyl acrylate, 4-hydroxybutyl acrylate and poly(ε-caprolactone) mono(meth)acrylate.

It is likewise possible to use the intrinsically known hydroxyl-containing epoxy (meth)acrylates having OH contents of 20 to 300 mg KOH/g or hydroxyl-containing polyurethane (meth)acrylates having OH contents of 20 to 300 mg KOH/g or acrylated polyacrylates having OH contents of 20 to 300 mg KOH/g and mixtures of these with one another, and mixtures with hydroxyl-containing unsaturated polyesters and mixtures with polyester (meth)acrylates or mixtures of hydroxyl-containing unsaturated polyesters with polyester (meth)acrylates.

Preference is given especially to urethane acrylates obtainable from the reaction of tris(p-isocyanatophenyl) thiophosphate and/or m-methylthiophenyl isocyanate with alcohol-functional acrylates such as hydroxyethyl (meth)acrylate, hydroxypropyl (meth)acrylate and/or hydroxybutyl (meth)acrylate.

It is likewise possible that the writing monomer comprises or consists of further unsaturated compounds such as α,β-unsaturated carboxylic acid derivatives, for example maleates, fumarates, maleimides, acrylamides, and also vinyl ethers, propenyl ethers, allyl ethers and compounds that contain dicyclopentadienyl units, and also olefinically unsaturated compounds, for example styrene, α-methylstyrene, vinyltoluene and/or olefins.

Photoinitiators of component d) are typically compounds activatable by actinic radiation that can trigger polymerization of the writing monomers. The photoinitiators can be distinguished between unimolecular (type I) and bimolecular (type II) initiators. In addition, they are distinguished in terms of their chemical nature into photoinitiators for free-radical, anionic, cationic or mixed modes of polymerization.

Type I photoinitiators (Norrish type I) for free-radical photopolymerization form free radicals on irradiation through unimolecular bond scission. Examples of type I photoinitiators are triazines, oximes, benzoin ethers, benzil ketals, bisimidazoles, aroylphosphine oxides, sulfonium salts and iodonium salts.

Type II photoinitiators (Norrish type II) for free-radical polymerization consist of a dye as sensitizer and a co-initiator, and undergo a bimolecular reaction on irradiation with light matched to the dye. The dye at first absorbs a photon and transmits energy to the co-initiator from an excited state. The latter releases the polymerization-triggering free radicals through electron or proton transfer or direct hydrogen abstraction.

In the context of this invention, preference is given to using type II photoinitiators.

Photoinitiator systems of this kind are described in principle in EP 0 223 587 A and preferably consist of a mixture of one or more dyes with the inventive compounds of the formula (IV).

Suitable dyes which form a type II photoinitiator together with a compound of the formula (IV) are the cationic dyes described in WO 2012062655, in combination with the anions that have just been described therein.

Cationic dyes are preferably understood to mean those of the following classes: acridine dyes, xanthene dyes, thioxanthene dyes, phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, externally cationic merocyanine dyes, externally cationic neutrocyanine dyes, zeromethine dyes—especially naphtholactam dyes, streptocyanine dyes. Dyes of this kind are described, for example, in H. Berneth in Ullmann's Encyclopedia of Industrial Chemistry, Azine Dyes, Wiley-VCH Verlag, 2008, H. Berneth in Ullmann's Encyclopedia of Industrial Chemistry, Methine Dyes and Pigments, Wiley-VCH Verlag, 2008, T. Gessner, U. Mayer in Ullmann's Encyclopedia of Industrial Chemistry, Triarylmethane and Diarylmethane Dyes, Wiley-VCH Verlag, 2000.

Particular preference is given to phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, zeromethine dyes—especially naphtholactam dyes, streptocyanine dyes.

Examples of cationic dyes are Astrazon Orange G, Basic Blue 3. Basic Orange 22, Basic Red 13, Basic Violet 7, Methylene Blue, New Methylene Blue, Azure A, 2,4-diphenyl-6-(4-methoxyphenyl)pyrylium, Safranin O, Astraphloxin, Brilliant Green, Crystal Violet, Ethyl Violet and thionine.

Preferred anions are especially $C_8$- to $C_{25}$-alkanesulfonate, preferably $C_{13}$- to $C_{25}$-alkanesulfonate, $C_3$- to $C_{18}$-perfluoroalkanesulfonate, $C_4$- to $C_{18}$-perfluoroalkanesulfonate bearing at least 3 hydrogen atoms in the alkyl chain, $C_9$- to $C_{25}$-alkanoate, $C_9$- to $C_{25}$-alkenoate, $C_8$- to $C_{25}$-alkylsulfate, preferably $C_{13}$- to $C_{25}$-alkylsulfate, $C_8$- to $C_{25}$-alkenylsulfate, preferably $C_{13}$- to $C_{25}$-alkenylsulfate, $C_3$- to $C_{18}$-perfluoroalkylsulfate, $C_4$- to $C_{18}$-perfluoroalkylsulfate bearing at least 3 hydrogen atoms in the alkyl chain, polyether sulfates based on at least 4 equivalents of ethylene oxide and/or 4 equivalents of propylene oxide, bis-$C_4$- to $C_{25}$-alkyl sulfosuccinate, $C_5$- to $C_7$-cycloalkyl sulfosuccinate, $C_3$- to $C_8$-alkenyl sulfosuccinate or $C_7$- to $C_{11}$-aralkyl sulfosuccinate, bis-$C_2$- to $C_{10}$-alkyl sulfosuccinate substituted by at least 8 fluorine atoms, $C_8$- to $C_{25}$-alkyl sulfoacetates, benzenesulfonate substituted by at least one radical from the group of halogen, $C_4$- to $C_{25}$-alkyl, perfluoro-$C_1$- to $C_8$-alkyl and/or $C_1$- to $C_{12}$-alkoxycarbonyl, naphthalene- or biphenylsulfonate optionally substituted by nitro, cyano, hydroxyl, $C_1$- to $C_{25}$-alkyl, $C_1$- to $C_{12}$-alkoxy, amino, $C_1$- to $C_{12}$-alkoxycarbonyl or chlorine, benzene-, naphthalene- or biphenyldisulfonate optionally substituted by nitro, cyano, hydroxyl, $C_1$- to $C_{25}$-alkyl, $C_1$- to $C_{12}$-alkoxy, $C_1$- to $C_{12}$-alkoxycarbonyl or chlorine, benzoate substituted by dinitro, $C_6$- to $C_{25}$-alkyl, $C_4$- to $C_{12}$-alkoxycarbonyl, benzoyl, chlorobenzoyl or tolyl, the anion of naphthalenedicarboxylic acid, diphenyl ether disulfonate, sulfonated or sulfated, optionally at least monounsaturated $C_8$ to $C_{25}$ fatty acid esters of aliphatic $C_1$ to $C_8$ alcohols or glycerol, bis(sulfo-$C_2$- to $C_6$-alkyl) $C_3$- to $C_{12}$-alkanedicarboxylates, bis(sulfo-$C_2$- to $C_6$-alkyl) itaconates, (sulfo-$C_2$- to $C_6$-alkyl) $C_6$- to $C_{18}$-alkanecarboxylates, sulfo-$C_2$- to $C_6$-alkyl acrylates or methacrylates, triscatechol phosphate optionally substituted by up to 12 halogen radicals, an anion from the group of tetraphenylborate, cyanotriphenylborate, tetraphenoxyborate, $C_4$- to $C_{12}$-alkyl-triphenylborate, the phenyl or phenoxy radicals of which may be substituted by halogen, $C_1$- to $C_4$-alkyl and/or $C_1$- to $C_4$-alkoxy, $C_4$- to $C_{12}$-alkyl trinaphthylborate, tetra-$C_1$- to $C_{20}$-alkoxyborate, 7,8- or 7,9-dicarbanidoundecaborate(1-) or (2-), optionally substituted on the boron and/or carbon atoms by one or two $C_1$- to $C_{12}$-alkyl or phenyl groups, dodecahydrodicarbadodecaborate(2-) or B—$C_1$- to $C_{12}$-alkyl-C-phenyldodecahydrodicarbadodecaborate(1-), where, in the case of polyvalent anions such as naphthalenedisulfonate, $A^-$ is one equivalent of this anion, and where the alkane and alkyl groups may be branched and/or substituted by halogen, cyano, methoxy, ethoxy, methoxycarbonyl or ethoxycarbonyl.

It is also preferable when the anion $A^-$ of the dye has an AClogP in the range from 1 to 30, more preferably in the range from 1 to 12 and especially preferably in the range from 1 to 6.5. AC log P is calculated according to J. Comput. Aid. Mol. Des. 2005, 19, 453; Virtual Computational Chemistry Laboratory, http://www.vcclab.org.

The photoinitiator system may also contain a further co-initiator, for example trichloromethyl initiators, aryl oxide initiators, bisimidazole initiators, ferrocene initiators, aminoalkyl initiators, oxime initiators, thiol initiators or peroxide initiators.

In a further preferred embodiment, the photopolymer formulation additionally contains urethanes as additives, in which case the urethanes may especially be substituted by at least one fluorine atom.

Preferably, the urethanes may have the general formula (VI)

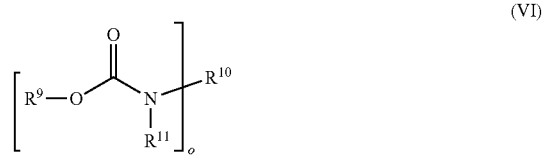

in which o≥1 and o≤8 and $R^9$, $R^{10}$ and $R^{11}$ are each a linear, branched, cyclic or heterocyclic organic moiety which is unsubstituted or else optionally substituted by heteroatoms and/or $R^{10}$, $R^{11}$ are each independently hydrogen, in which case preferably at least one of the $R^9$, $R^{10}$, $R^{11}$ radicals is substituted by at least one fluorine atom and, more preferably, $R^9$ is an organic radical having at least one fluorine atom. More preferably, $R^{11}$ is a linear, branched, cyclic or heterocyclic organic moiety which is unsubstituted or else optionally substituted by heteroatoms, for example fluorine.

The present invention further provides a photopolymer comprising a photopolymer formulation, especially comprising matrix polymers, a writing monomer and a photoinitiator system additionally comprising a compound of the formula (IV) obtainable or obtained by the process according to the invention or a compound of the formula (C).

The above remarks concerning further preferred embodiments of the photopolymer forulation according to the invention also apply mutatis mutandis to the photopolymer according to the invention.

A holographic medium likewise becomes obtainable, especially in the form of a film comprising a photopolymer according to the invention or obtainable by using a photopolymer formulation according to the invention. The photopolymer composition is also usable for production of holographic media.

It is possible to expose holographic information into such holographic media.

The holographic media according to the invention can be processed by corresponding exposure processes for optical applications throughout the entire visible and near-UV range (300-800 nm) to give holograms. Visual holograms include all holograms that can be recorded by processes known to those skilled in the art. These include in-line (Gabor) holograms, off-axis holograms, full-aperture transfer holograms, white light transmission holograms ("rainbow holograms"), Denisyuk holograms, off-axis reflection holograms, edge-lit holograms and holographic stereograms. Preference is given to reflection holograms, Denisyuk holograms, transmission holograms.

Possible optical functions of the holograms which can be produced with the photopolymer formulations according to the invention correspond to the optical functions of light elements such as lenses, mirrors, deflecting mirrors, filters, diffuser lenses, diffraction elements, diffusers, light guides, waveguides, projection lenses and/or masks. It is likewise possible for combinations of these optical functions to be combined in one hologram independently of each other. Frequently, these optical elements exhibit frequency selectivity, according to how the holograms have been exposed and the dimensions of the hologram.

In addition, it is also possible by means of the holographic media to produce holographic images or diagrams, for example for personal portraits, biometric representations in security documents, or generally images or image structures for advertising, security labels, brand protection, branding, labels, design elements, decorations, illustrations, collectible cards, pictures and the like, and pictures that can represent digital data, including in combination with the products detailed above. Holographic images can have the impression of a three-dimensional image, or else they can represent image sequences, short films or a number of different objects, according to the angle from which and the light source with which (including moving light sources) etc. they are illuminated. Because of this variety of possible designs, holograms, especially volume holograms, constitute an attractive technical solution for the abovementioned application.

The holographic media can be used for recording of in-line, off-axis, full-aperture transfer, white light transmission, Denisyuk, off-axis reflection or edge-lit holograms and also of holographic stereograms, especially for production of optical elements, images or image representations.

Holograms are obtainable from the holographic media according to the invention.

The examples which follow serve to illustrate the invention, without restricting it thereto.

BRIEF DESCRIPTION OF THE DRAWINGS

FIG. 1 shows the holographic properties Δn of the holographic media determined by means of twin-beam interference in reflection arrangement as described in WO2015091427.

EXAMPLES

Test methods:
OH number: The OH numbers reported were determined according to DIN 53240-2.
NCO value: The NCO values (isocyanate contents) reported were determined according to DIN EN ISO 11909.
Solids content: The solids contents reported were determined according to DIN EN ISO 3251.
Refractive index modulation Δn: The holographic properties Δn of the holographic media were determined by means of twin-beam interference in reflection arrangement as described in WO2015091427; a representative result is shown in FIG. 1.
Substances
The solvents, reagents and all bromoaromatics used were purchased from chemical suppliers. Anhydrous solvents contain <50 ppm of water.

| | |
|---|---|
| Ethylboronic acid pinacol ester | [82954-89-0] is available from TCI Europe N.V., Zwijndrecht, Belgium. |
| Isopropylboronic acid pinacol ester | [76347-13-2] is available from ABCR GmbH & Co. KG, Karlsruhe, Germany. |
| 2-Isopropenylboronic acid pinacol ester | [126726-62-3] is available from ABCR GmbH & Co. KG, Karlsruhe, Germany. |
| l-Dodecylboronic acid pinacol ester | [177035-82-4] is available from ABCR GmbH & Co. KG, Karlsruhe, Germany. |
| 3-Phenyl-1-propyl boronic acid pinacol ester | [329685-40-7] is available from ABCR GmbH & Co. KG, Karlsruhe, Germany. |
| Diisopropyl allyl boronate | [51851-79-7] is available from ABCR GmbH & Co. KG, Karlsruhe, Germany. |
| (1,3,2-Dioxaborinan-2-yl)cyclohexane | [30169-75-6] is available from ABCR GmbH & Co. KG, Karlsruhe, Germany. |
| Dibromoborane-dimethyl sulfide complex | [55671-55-1] is available from Aldrich Chemie, Steinheim, Germany. |
| 1-Octadecene | [112-41-4] is available from ABCR GmbH & Co. KG, Karlsruhe, Germany. |
| Desmorapid Z | dibutyltin dilaurate [77-58-7], product from Covestro AG, Leverkusen, Germany. |
| Desmodur ® N 3900 | product from Covestro AG, Leverkusen, DE, hexane diisocyanate-based polyisocyanate, proportion of iminooxadiazinedione at least 30%, NCO content: 23.5%. |
| Fomrez UL 28 | Urethanization catalyst, commercial product of Momentive Performance Chemicals, Wilton, CT, USA. |

Lewatit® MDS TP 208 is available from Lanxess Deutschland GmbH, Cologne, Germany.

2-Hexyl-1,3,2-dioxaborinane [86290-24-6] was prepared as described in Organometallics 1983, 2 (10), p. 1311-16, DOI:10.1021/om5.0004a008 from 1-hexene, propane-1,3-diol and dibromoborane-dimethyl sulfide complex.

2-Octadecyl-4,4,5,5-tetramethyl-1,3,2-dioxaborolane was prepared analogously to Organometallics 1983, 2 (10), p. 1311-16, DOI:10.1021/om5.0004a008 from 1-octadecene, propane-1,3-diol and dibromoborane-dimethyl sulfide complex.

Dye 1 (3,7-bis(diethylamino)phenoxazin-5-ium bis(2-ethylhexyl)sulfosuccinate) was prepared as described in WO 2012062655.

Polyol 1 was prepared as described in Polyol 1 in WO2015091427.

Urethane acrylate 1 (phosphorothioyltris(oxybenzene-4,1-diylcarbamoyloxyethane-2,1-diyl) trisacrylate, [1072454-85-3]) was prepared as described in WO2015091427.

Urethane acrylate 2 (2-({[3-(methylsulfanyl)phenyl]carbamoyl}oxy)ethyl prop-2-enoate, [1207339-61-4]) was prepared as described in WO2015091427.

Additive 1, bis(2,2,3,3,4,4,5,5,6,6,7,7-dodecafluoroheptyl)-(2,2,4-trimethylhexane-1,6-diyl)biscarbamate [1799437-41-4] was prepared as described in WO2015091427.

Origin of the $1/n\ K^{n+}$ cations used

The $1/n\ K^{n+}$ cations specified in Table 1 were purchased from the chemical supplier mentioned or prepared according to the source mentioned or the preparation is described hereinafter.

TABLE 1

Overview of the cations of the formula (II) used

| Index | Name | Structure | CAS | Source |
|---|---|---|---|---|
| K-1 | Tetramethylammonium bromide | Me$_4$NBr | [64-20-0] | 426296, Aldrich |
| K-2 | Tetrabutylammonium bromide | Bu$_4$NBr | [1643-19-2] | 426288, Aldrich |
| K-3 | Benzyldimethylhexadecyl-ammonium chloride | BnMe$_2$HexadecylNCl | [122-18-9] | AB252026, abcr GmbH |
| K-4 | Hexadecyltrimethylammonium bromide | 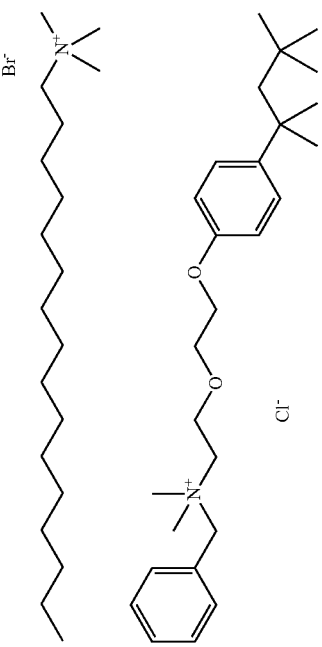 | [57-09-0] | AB117004, abcr GmbH |
| K-5 | Benzethonium chloride | 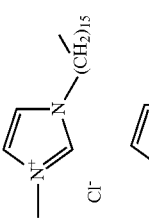 | [121-54-0] | AB131627, abcr GmbH |
| K-6 | 1-Hexadecyl-3-methylimidazolium chloride | 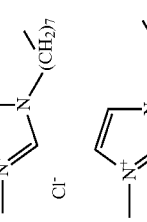 | [61546-01-8] | AB289677, abcr GmbH |
| K-7 | 1-Methyl-3-octylimidazolium chloride | 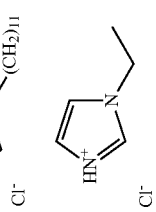 | [64697-40-1] | AB289637, abcr GmbH |
| K-8 | 1-Dodecyl-3-methylimidazolium chloride | 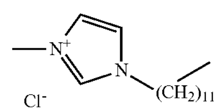 | [114569-84-5] | AB280681, abcr GmbH |
| K-9 | 1-Ethyl-3-imidazolium chloride | 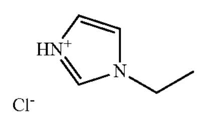 | [81505-35-3] | AB289800, abcr GmbH |

TABLE 1-continued

Overview of the cations of the formula (II) used

| Index | Name | Structure | CAS | Source |
|---|---|---|---|---|
| K-10 | 1-Benzyl-3-hexadecyl-imidazolium bromide | 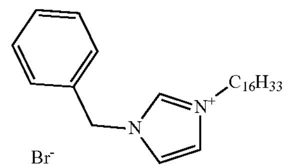 | [1224595-52-1] | Fuel Processing Technology (2014), 118, 296-301. |
| K-11 | N-Hexadecylpyridinium chloride monohydrate | 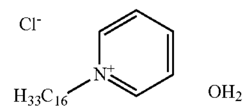 | [6004-24-6] | AB117002, abcr GmbH |
| K-12 | N-Docosylpyridinium bromide | 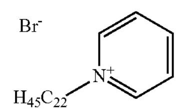 | [80039-83-4] | J. Am. Chem. Soc. (2002), 124 (11), 2604-2613. |
| K-13 | 4-tert-Butyl-1-hexadecyl-pyridinium chloride | 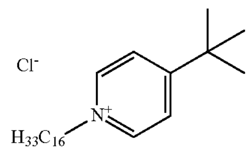 | [1702465-32-4] | WO 201505576 A1 |
| K-14 | 1,1'-[1,3-Phenylenebis(methylene)bis(pyridinium) dichloride | 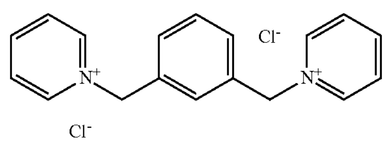 [SMILES: c1cc[n+](Cc2cccc(C[n+]3ccccc3)c2)cc1 ; [Cl-] ; [Cl-]] | [84002-71-1] | Zhurnal Neorganicheskoi Khimii (1978), 23, 825-6. |
| K-15 | N,N,N',N',N',N'-Hexaethyl-1,3-benzenedimethane aminium dibromide | 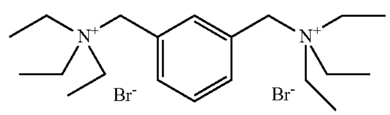 [SMILES: CC[N+](CC)(CC)Cc1cccc(C[N+](CC)(CC)CC)c1 ; [Br-] ; [Br-]] | [66753-59-1P] | Chemische Berichte (1984), 117 (4), 1487-96. |
| K-16 | N,N-Dioctadecylpiperidium chloride | 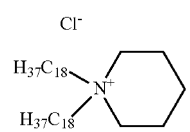 | [61550-95-6] | J. Am. Chem. Soc. (1955), 77, 485-6. |

TABLE 1-continued

Overview of the cations of the formula (II) used

| Index | Name | Structure | CAS | Source |
|---|---|---|---|---|
| K-17 | N-Hexadecyl-N,N-dimethylanilinium bromide | 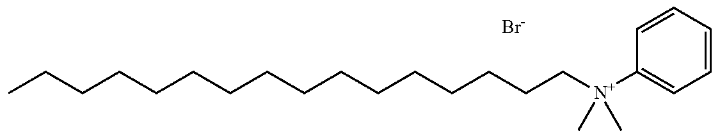 [SMILES: CCCCCCCCCCCCCCCC[N+](C)(C)c1ccccc1 ; [Br-]] | [17695-00-0] | Taiwan Kexue (1959), 13, 95-8. |
| K-18 | N,N,N',N',N',N'-Hexabutyl-hexamethylenediammonium dibromide | 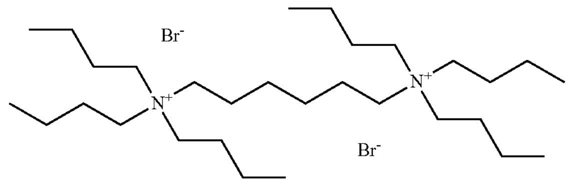 [SMILES: CCCC[N+](CCCC)(CCCC)CCCCCC[N+](CCCC)(CCCC)CCCC ; [Br-] ; [Br-]] | [745829-82-7P] | Chemical Engineering Science, 69 (1), 483-491. |
| K-19 | N-(2-(Benzoyloxy)ethyl)-N,N-dimethyloctadecane-1-aminium bromide | 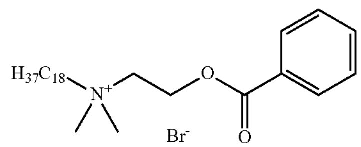 | [152167-30-1] | U.S. Pat. No. 5,194,472 A |
| K-20 | N-(2-((2-Ethylhexanoyl)oxy)ethyl)-N,N-dimethylhexadecane-1-aminium bromide | 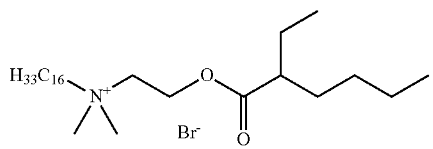 | | For preparation method see below |
| K-21 | N-Benzyl-N,N-dimethyl-2-(2-(palmitoyloxy)ethoxy)ethane-1-aminium bromide | 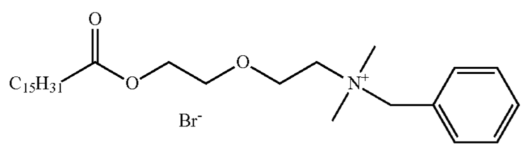 | | For preparation method see below |
| K-22 | 2-(Benzoyloxy)-N,N-dimethyl-N-(2-(palmitoyloxy)ethyl)ethane-1-aminium bromide | 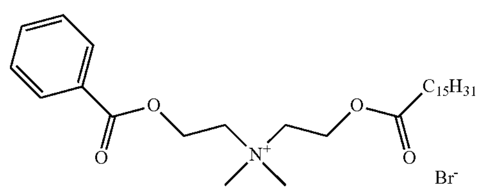 | | For preparation method see below |

TABLE 1-continued

Overview of the cations of the formula (II) used

| Index | Name | Structure | CAS | Source |
|---|---|---|---|---|
| K-23 | N-(3-((2-Ethylhexyl)oxy)-3-oxopropyl)-N,N-dimethyloctadecane-1-aminium bromide | 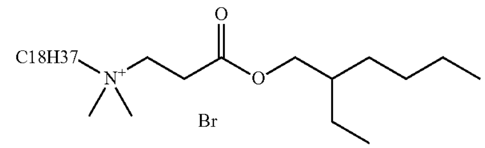 | | For preparation method see below |
| K-24 | N-(2-((Hexylcarbamoyl)oxy)ethyl)-N,N-dimethylhexadecane-1-aminium bromide | 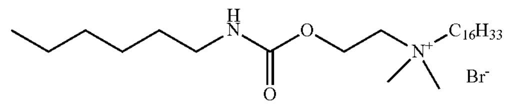 | | For preparation method see below |
| K-25 | $N^1,N^{16}$-Dihexadecyl-$N^1,N^1,N^{16},N^{16}$-7,7,10-heptamethyl-4,13-dioxo-3,14-dioxa-5,12-diazahexadecane-1,16-diaminium dibromide | 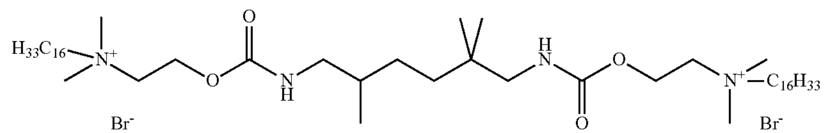 | | For preparation method see below |
| K-26 | N-(2-((((5-(((2-(Hexadecyldimethylammonio)ethoxy)carbonyl)amino)-1,3,3-trimethylcyclohexyl)methyl)carbamoyl)oxy)ethyl)-N,N-dimethylhexadecane-1-aminium dibromide | 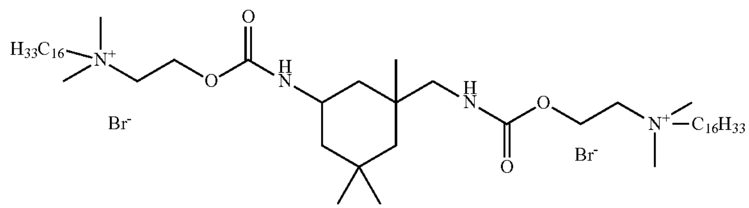 | | For preparation method see below |
| K-27 | N,N'-(((((Methylenebis(cyclohexane-4,1-diyl))bis(azanediyl))bis(carbonyl))bis(oxy))bis(ethane-2,1-diyl))bis(N,N-dimethylhexadecane-1-aminium) dibromide | 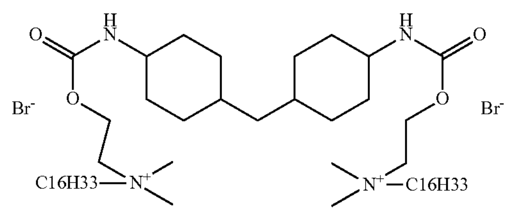 | | For preparation method see below |

TABLE 1-continued

Overview of the cations of the formula (II) used

| Index | Name | Structure | CAS | Source |
|---|---|---|---|---|
| K-28 | N,N'-((((4-Methyl-1,3-phenylene)bis(azanediyl))bis(carbonyl))bis(oxy))bis(ethane-2,1-diyl))bis(N,N-dimethylhexadecane-1-aminium) dibromide | 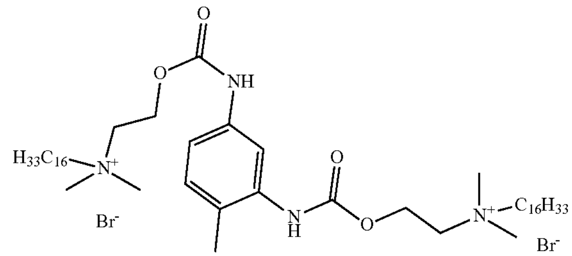 | [1073535-73-5] | For preparation method see below |
| K-29 | N,N'-((((Methylenebis(4,1-phenylene)bis(azanediyl))bis(carbonyl))bis(oxy))bis(ethane-2,1-diyl))bis(N,N-dimethylhexadecane-1-aminium) dibromide | 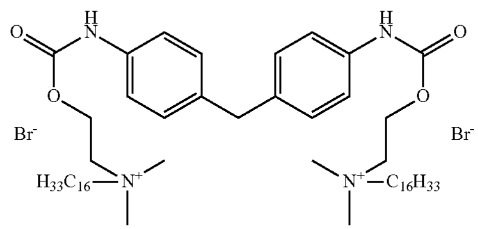 | | For preparation method see below |
| K-30 | N-(2-(2-((Hexylcarbamoyl)oxy)ethoxy)ethyl)-N,N-dimethylhexadecane-1-aminium bromide | 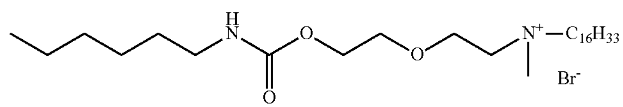 | | For preparation method see below |
| K-31 | N$^1$,N$^{22}$-Dihexadecyl-N$^1$,N$^1$,N$^{22}$,N$^{22}$,10,10,13-heptamethyl-7,16-dioxo-3,6,17,20-tetraoxa-8,15-diazadocosane-1,22-diaminium dibromide | 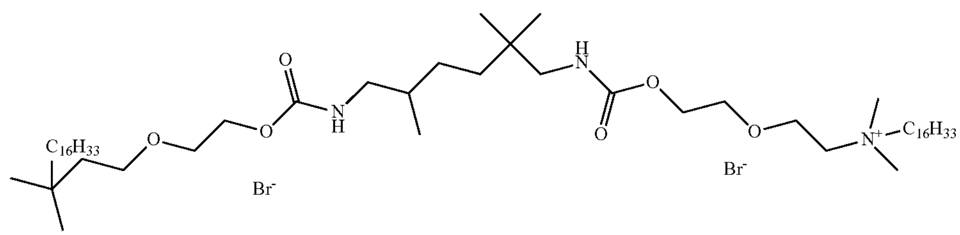 | | For preparation method see below |

TABLE 1-continued

Overview of the cations of the formula (II) used

| Index | Name | Structure | CAS | Source |
|---|---|---|---|---|
| K-32 | N-(2-(2-(((3-(10,10-Dimethyl-3-oxo-4,7-dioxa-2,10-diazahexacosan-10-ium-1-yl)-3,5,5-trimethylcyclohexyl)carbamoyl)oxy)ethoxy)ethyl)-N,N-dimethylhexadecane-1-aminium dibromide | 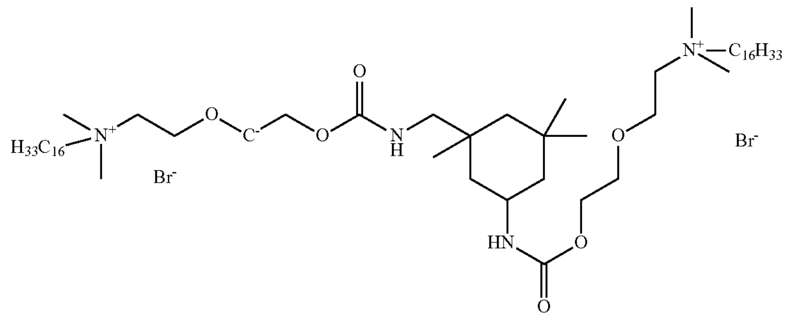 | | For preparation method see below |
| K-33 | N,N'-((((((Methylenebis(cyclohexane-4,1-diyl))bis(azanediyl))bis(carbonyl))bis(oxy))bis(ethane-2,1-diyl))bis((oxy))bis(ethane-1,2-diyl))bis(N,N-dimethylhexadecane-1-aminium) dibromide | 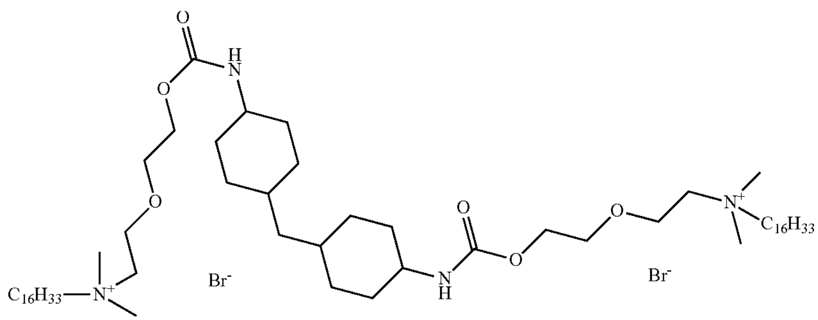 | | For preparation method see below |
| K-34 | N,N'-((((((4-Methyl-1,3-phenylene)bis(azanediyl))bis-(carbonyl))bis(oxy))bis(ethane-2,1-diyl)bis(oxy))bis(ethane-2,1-diyl))bis(N,N-dimethylhexadecane-1-aminium) dibromide | 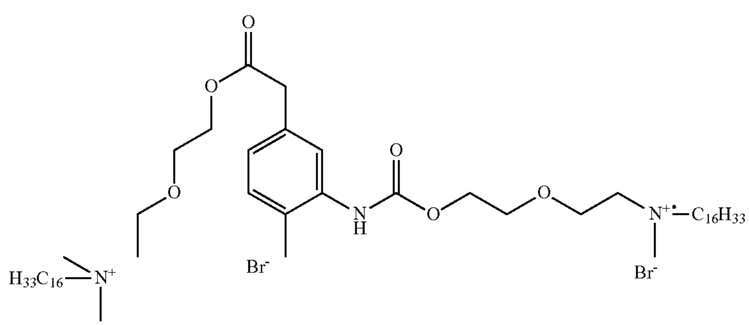 | | For preparation method see below |

TABLE 1-continued

Overview of the cations of the formula (II) used

| Index | Name | Structure | CAS | Source |
|---|---|---|---|---|
| K-35 | N,N'-(((((Methylenebis(4,1-phenylene))bis((azenediyl))bis(carbonyl))bis(oxy))bis(ethane-2,1-diyl))bis(oxy)bis(ethane-2,1-diyl))bis(N,N-dimethylhexadecane-1-aminium) dibromide | 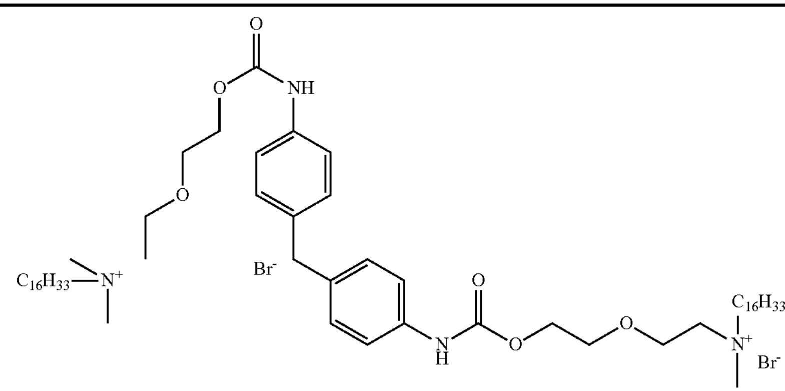 | | For preparation method see below |
| K-36 | $N^1,N^1,N^1,N^3,N^3,N^3,N^5,N^5,N^5$-Nonamethyl-1,3,5-benzenetrimethanaminium triiodide | 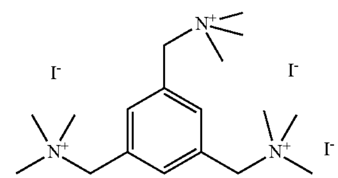 | [88888-13-5] | Chem. Ber. 177, 1487-1496 (1984). |
| K-37 | N-[2-[2-(Benzoyloxy)ethoxy]ethoxy]ethyl]-N,N-dimethyloctadecane-1-aminium bromide | 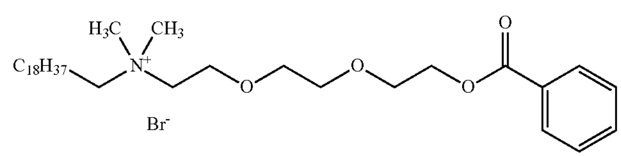 | [215591-20-1] | SK 278487 |
| K-38 | 1-[3-[(2-Ethylhexyl)oxy]-3-oxopropyl]-4-methylpyridinium chloride | 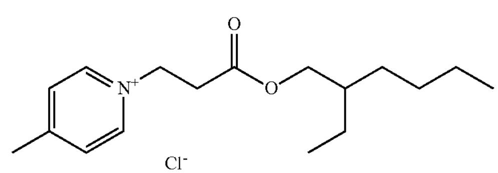 [SMILES: CCCCC(CC)COC(=O)CC[n+]1ccc(C)cc1 ; [Cl-]] | [110250-87-8] | U.S. Pat. No. 2,857,310 |

TABLE 1-continued

Overview of the cations of the formula (II) used

| Index | Name | Structure | CAS | Source |
|---|---|---|---|---|
| K-39 | 4-Methyl-1-[2-[(1-oxotetradecyl)oxy]ethyl]pyridinium chloride | 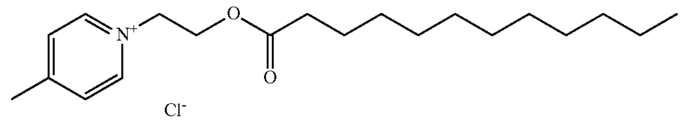 [SMILES: CCCCCCCCCCCC(=O)OCC[n+]1ccc(C)cc1 ; [Cl-]] | [42936-94-7] | Izvestiya Vysshikh Uchebnykh Zavedenii, Khimiyai Khimicheskaya Tekhnologiya (1973), 16(6), 891. |
| K-40 | 1-[[3-(4-Methoxyphenyl)-2-oxo-5-oxazolidinyl]methyl]-4-phenyl-pyridinium bromide | 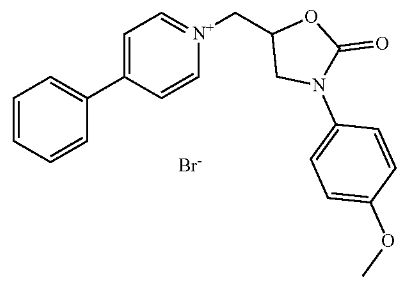 [SMILES: COc1ccc(N2CC(C[n+]3ccc(-c4ccccc4)cc3)OC2=O)cc1 ; [Br-]] | [121082-85-7] | DE 3723797 |
| K-41 | 4-Methyl-1-[2-[(1-oxodecyl)amino]ethyl]pyridinium chloride | 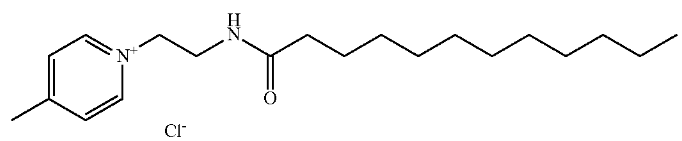 [SMILES: CCCCCCCCCCCC(=O)NCC[n+]1ccc(C)cc1 ; [Cl-]] | [15147-43-0] | Chemicky-Prumysl (1967), 17(2), 67-9. |
| K-42 | 4,5-Dihydro-1-methyl-3-[2-[(1-oxotetradecyl)oxy]ethyl]-2-pentadecyl-1H-imidazolium chloride | 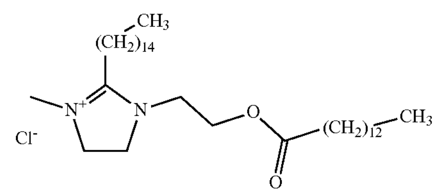 | [131625-89-3] | U.S. Pat. No. 4,954,635 |
| K-43 | 4,4-Bis[2-[[(9Z)-1-oxo-9-octadecen-1-yl]oxy]ethyl]morpholinium chloride | 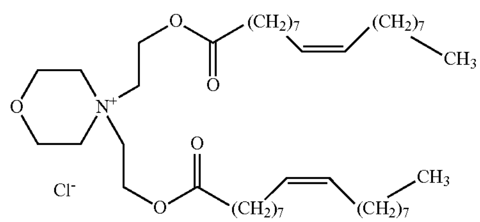 | [272462-96-1] | WO200030444 |

TABLE 1-continued

Overview of the cations of the formula (II) used

| Index | Name | Structure | CAS | Source |
|---|---|---|---|---|
| K-100 | Tributyltetradecylphosphonium chloride | 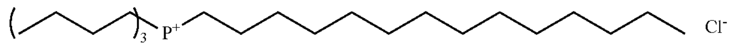 | [81741-28-8] | P444(14) Cl, Ionic Liquids Technologies GmbH |
| K-101 | Trihexyltetradecylphosphonium chloride | 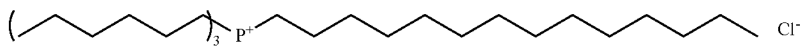 | [258864-54-9] | P666(14) Cl, Ionic Liquids Technologies GmbH |
| K-102 | Methyltriphenylphosphonium chloride | 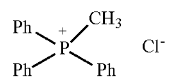 | [1031-15-8] | AB349191, abcr GmbH |
| K-103 | Triphenylbenzylphosphonium chloride | 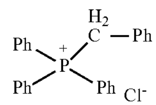 | [1100-88-5] | AB113982, abcr GmbH |
| K-104 | Tetraphenylphosphonium chloride | 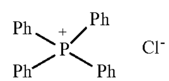 | [2001-45-8] | AB119018, abcr GmbH |
| K-105 | Allyltriphenylphosphonium bromide | 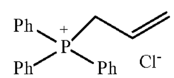 | [1560-54-9] | AB121395, abcr GmbH |
| K-106 | (2-Oxo-2-phenylethyl)triphenylphosphonium bromide | 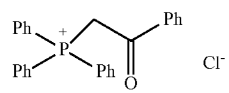 | [6048-29-9] | AB233312, abcr GmbH |
| K-200 | 4-Methyl-2,6-diphenylpyrylium tetrafluoroborate | 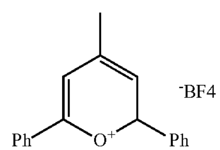 [SMILES: CC1=CC(c2ccccc2)[OH+]C(c2ccccc2)=C1] | [2340-23-0] | S919802, Aldrich |
| K-201 | 2,4,6-Triphenylpyrylium tetrafluoroborate | 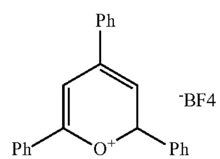 [SMILES: C1=C(c2ccccc2)C=C(c2ccccc2)[OH+]C1c1ccccc1] | [448-61-3] | AB119969, abcr GmbH |

TABLE 1-continued

Overview of the cations of the formula (II) used

| Index | Name | Structure | CAS | Source |
|---|---|---|---|---|
| K-202 | 2,4,6-Trimethylpyrylium tetrafluoroborate | 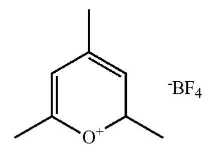 | [773-01-3] | AB177250, abcr GmbH |
| K-203 | 4,4'-Bis(2,6-diphenylpyrylium tetrafluoroborate) | 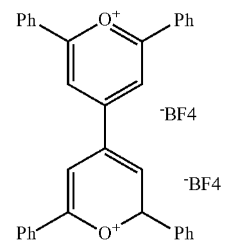 [SMILES: C1=C(c2cc(-c3ccccc3)[o+]c(-c3ccccc3)c2)C=C(c2ccccc2)[OH+]C1c1ccccc1] | [42559-29-5] | S873950, Aldrich |
| K-300 | Diphenyl[4-(phenylthio)phenyl]sulfonium hexafluorophosphate | 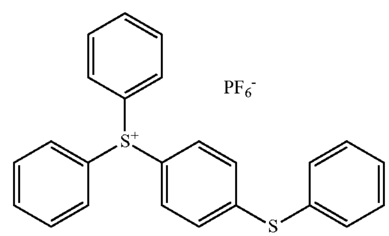 | [75482-18-7] | AB334122, abcr GmbH |
| K-301 | Bis(diphenylsulfonium)diphenyl thioether hexafluorophosphate | 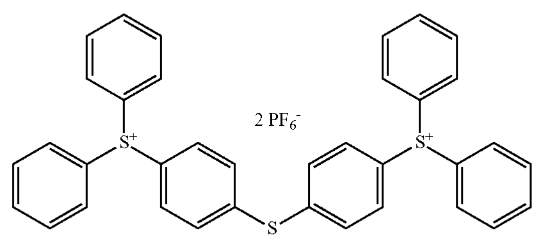 | [74227-35-3] | AB134315, abcr GmbH |

TABLE 1-continued

Overview of the cations of the formula (II) used

| Index | Name | Structure | CAS | Source |
|---|---|---|---|---|
| K-302 | Diphenyl[4-(phenylthio)phenyl] sulfonium triflate | 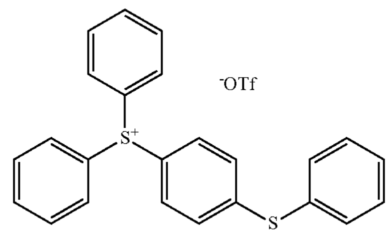 [SMILES: c1ccc(Sc2ccc([S+](c3ccccc3)c3ccccc3)cc2)cc1 ; "-OTf"] | [111281-12-0] | AB231614, abcr GmbH |
| K-303 | Mixture of K-300 + K-301 (Cyracure UVI 6990) | | [104558-95-4] | BASF SE, Ludwigshafen, Germany |
| K-304 | Tris[4-[(4-acetylphenyl)thio]phenyl] sulfonium tris[(trifluoromethyl) sulfonyl]methanide | 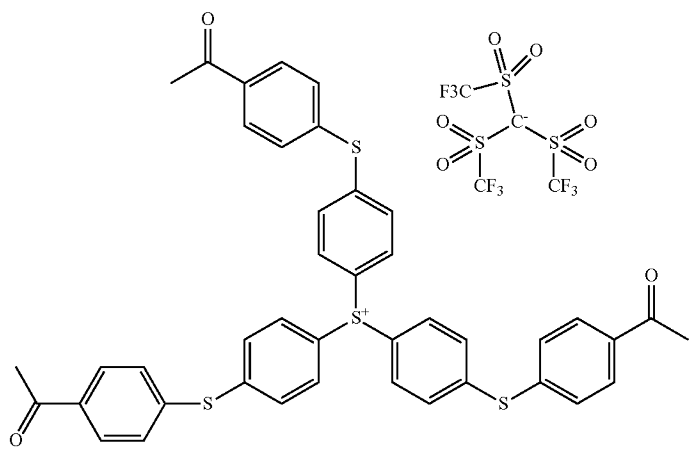 [SMILES: CC(=O)c1ccc(Sc2ccc([S+](c3ccc(Sc4ccc(C(C)=O)cc4)cc3)c3ccc(Sc4ccc(C(C)=O)cc4)cc3)cc2)cc1 ; O=S(=O)([C-](S(=O)(=O)C(F)(F)F)S(=O)(=O)C(F)(F)F)C(F)(F)F] | [953084-20-3] | BASF SE, Ludwigshafen, Germany |
| K-305 | 2,4,6-Triphenylthiopyrylium perchlorate | 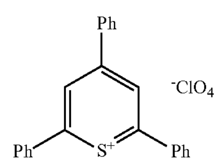 | [2930-37-2] | AKOS001017031, AKos GmbH Austr. 26 Steinen, D-79585 Germany |

TABLE 1-continued

Overview of the cations of the formula (II) used

| Index | Name | Structure | CAS | Source |
|---|---|---|---|---|
| K-400 | (4-Methylphenyl)[4-(2-methylpropyl)phenyl]iodonium hexafluorophosphate | 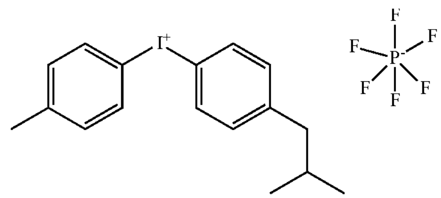 [SMILES: Cc1ccc([I+]c2ccc(CC(C)C)cc2)cc1 ; F[P-](F)(F)(F)(F)F] | [344562-80-7] | BASF SE, Ludwigshafen, Germany |
| K-401 | Diphenyliodonium chloride | 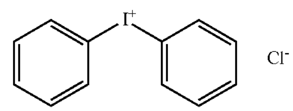 [SMILES: c1ccc([I+]c2ccccc2)cc1 ; [Cl-]] | [1483-72-3] | AB109613, abcr GmbH |
| K-402 | Bis(4-methylphenyl)iodonium hexafluorophosphate | 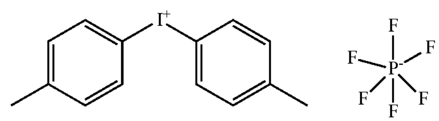 | [60565-88-0] | AB336755, abcr GmbH |
| K-403 | Diphenyleneiodonium chloride | 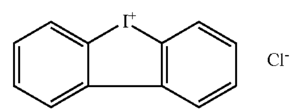 [SMILES: c1ccc2c(c1)[I+]c1ccccc1-2 ; [Cl-]] | [4673-26-1] | AB348986, abcr GmbH |

Preparation of Commercially Unavailable Cations 1/n K"+

N-(2-((2-Ethylhexanoyl)oxy)ethyl)-N,N-dimethylhexadecane-1-aminium bromide (K-20)

5.00 g of N,N-dimethylethanolamine were initially charged in dry chloroform cooled with an ice bath, and 9.12 g of 2-ethylhexanoyl chloride were cautiously added dropwise and the mixture was stirred at room temperature for 30 min. 30 ml of saturated sodium hydrogencarbonate solution were added and the organic solution was extracted with saturated sodium hydrogencarbonate solution until it was chloride-free. Subsequently, the organic phase was washed with 30 ml of water, the solution was dried and the solvent was distilled off under reduced pressure. 10.99 g of amino ester were obtained.

To a solution of 10.99 g of amino ester in 30 ml of acetonitrile were added 15.58 g of 1-bromohexadecane, and the mixture was heated at reflux for 6 h. The solvent was almost completely distilled off under reduced pressure, the precipitated solids were isolated, and 19.33 g of a colourless tacky resin were obtained.

N-Benzyl-N,N-dimethyl-2-(2-(palmitoyloxy)ethoxy)ethane-1-aminium bromide (K-21)

6.00 g of N,N-2-[2-(dimethylamino)ethoxy]ethanol were initially charged in dry chloroform cooled with an ice bath, and 12.38 g of hexadecanoyl chloride were cautiously added dropwise and the mixture was stirred at room temperature for 30 min. 30 ml of saturated sodium hydrogencarbonate solution were added and the organic solution was extracted with saturated sodium hydrogencarbonate solution until it was chloride-free. Subsequently, the organic phase was washed with 30 ml of water, the solution was dried and the solvent was distilled off under reduced pressure. 14.68 g of amino ester were obtained.

To a solution of 14.68 g of amino ester in 30 ml of acetonitrile were added 6.77 g of benzyl bromide, and the mixture was heated at reflux for 6 h. The solvent was almost completely distilled off under reduced pressure, the precipitated solids were isolated, and 8.23 g of a colourless tacky resin were obtained.

2-(Benzyloxy)-N,N-dimethyl-N-(2-(palmitoyloxy)ethyl)ethane-1-aminium bromide (K-22)

6.00 g of N,N-2-[2-(dimethylamino)ethoxy]ethanol were initially charged in dry chloroform cooled with an ice bath, and 12.38 g of hexadecanoyl chloride were cautiously added dropwise and the mixture was stirred at room temperature for 30 min. 30 ml of saturated sodium hydrogencarbonate solution were added and the organic solution was extracted with saturated sodium hydrogencarbonate solution until it was chloride-free. Subsequently, the organic phase was washed with 30 ml of water, the solution was dried and the solvent was distilled off under reduced pressure. 14.68 g of amino ester were obtained.

To a solution of 14.68 g of amino ester in 30 ml of acetonitrile were added 6.77 g of benzyl bromide, and the mixture was heated at reflux for 6 h. The solvent was almost completely distilled off under reduced pressure, the precipitated solids were isolated, and 8.23 g of a colourless tacky resin were obtained.

N-(3-((2-Ethylhexyl)oxy)-3-oxopropyl)-N,N-dimethyloctadecane-1-aminium bromide (K-23)

To a solution of 10.0 g of N,N-dimethyl-β-alanine 2-ethylhexyl ester ([184244-48-2], prepared as described in U.S. Pat. No. 5,565,290 A) in 30 ml of acetonitrile were added 15.0 g of octadecyl bromide and the mixture was heated at reflux for 6 h. The solvent was almost completely distilled off under reduced pressure, and 24.50 g of a colourless oil were obtained.

N-(2-((Hexylcarbamoyl)oxy)ethyl)-N,N-dimethylhexadecane-1-aminium bromide (K-24)

To a mixture of 29.4 g of hexyl isocyanate and 0.05 g of Desmorapid Z were added dropwise, at 60° C., 20.6 g of N,N-dimethylethanol, and the mixture was kept at this temperature for 8 h. After cooling to room temperature, 50.0 g of aminourethane were obtained.

50.0 g of aminourethane were dissolved in 120 ml of acetonitrile, 70.6 g of 1-bromohexadecane were added dropwise and the mixture was heated at reflux for 12 h. The precipitated solids were isolated, washed with cold ether and dried, and 115.0 g of a colourless tacky resin were obtained.

$N^1,N^{16}$-Dihexadecyl-$N^1,N^1,N^{16},N^{16}$,7,7,10-heptamethyl-4,13-dioxo-3,14-dioxa-5,12-diazahexadecane-1,16-diaminium dibromide (K-25)

To a mixture of 27.0 g of Vestanat TMDI (product from EVONIK Deutschland) and 0.05 g of Desmorapid Z were added dropwise, at 60° C., 22.9 g of N,N-dimethylethanol, and the mixture was kept at this temperature for 8 h. After cooling to room temperature, 50.0 g of aminourethane were obtained.

11.7 g of aminourethane were dissolved in 50 ml of acetonitrile, 18.3 g of 1-bromohexadecane were added dropwise and the mixture was heated at reflux for 12 h. The precipitated solids were isolated, washed with cold ether and dried, and 28.0 g of a colourless tacky resin were obtained.

N-(2-(((5-(((2-(Hexadecyldimethylammonio)ethoxy)carbonyl)amino)-1,3,3-trimethylcyclohexyl)methyl)carbamoyl)oxy)ethyl)-N,N-dimethylhexadecane-1-aminium dibromide (K-26)

To a mixture of 27.7 g of Desmodur I (product from COVESTRO Deutschland) and 0.05 g of Desmorapid Z were added dropwise, at 60° C., 22.2 g of N,N-dimethylethanol, and the mixture was kept at this temperature for 8 h. After cooling to room temperature, 50.0 g of aminourethane were obtained.

11.9 g of aminourethane were dissolved in 50 ml of acetonitrile, 18.1 g of 1-bromohexadecane were added dropwise and the mixture was heated at reflux for 12 h. The precipitated solids were isolated, washed with cold ether and dried, and 29.3 g of a colourless tacky resin were obtained.

N,N'-(((((Methylenebis(cyclohexane-4,1-diyl))bis(azanediyl))bis(carbonyl))bis(oxy))bis(ethane-2,1-diyl))bis(N,N-dimethylhexadecane-1-aminium) dibromide (K-27)

To a mixture of 29.7 g of Desmodur W (product from COVESTRO Deutschland) and 0.05 g of Desmorapid Z were added dropwise, at 60° C., 20.2 g of N,N-dimethylethanol, and the mixture was kept at this temperature for 8 h. After cooling to room temperature, 50.0 g of aminourethane were obtained.

12.6 g of aminourethane were dissolved in 50 ml of acetonitrile, 17.4 g of 1-bromohexadecane were added dropwise and the mixture was heated at reflux for 12 h. The precipitated solids were isolated, washed with cold ether and dried, and 28.9 g of a colourless tacky resin were obtained.

N,N'-(((((4-Methyl-1,3-phenylene)bis(azanediyl))bis
(carbonyl))bis(oxy))bis(ethane-2,1-diyl))bis(N,N-
dimethylhexadecane-1-aminium) dibromide (K-28)

To a mixture of 24.7 g of Desmodur T80 (product from COVESTRO Deutschland) and 0.05 g of Desmorapid Z were added dropwise, at 10° C., 25.3 g of N,N-dimethylethanol, and, on completion of addition, the mixture was kept at 60° C. for 8 h. After cooling to room temperature, 50.0 g of aminourethane were obtained.

11.0 g of aminourethane were dissolved in 50 ml of acetonitrile, 19.0 g of 1-bromohexadecane were added dropwise and the mixture was heated at reflux for 12 h. The precipitated solids were isolated, washed with cold ether and dried, and 27.2 g of a colourless tacky resin were obtained.

N,N'-(((((Methylenebis(4,1-phenylene))bis(azanediyl))
bis(carbonyl))bis(oxy))bis(ethane-2,1-diyl))bis(N,N-dim-
ethylhexadecane-1-aminium) dibromide (K-29)

To a mixture of 29.2 g of Desmodur MDI (product from COVESTRO Deutschland) and 0.05 g of Desmorapid Z were added dropwise, at 10° C., 20.8 g of N,N-dimethylethanol, and, on completion of addition, the mixture was kept at 60° C. for 8 h. After cooling to room temperature, 50.0 g of aminourethane were obtained.

12.4 g of aminourethane were dissolved in 50 ml of acetonitrile, 17.6 g of 1-bromohexadecane were added dropwise and the mixture was heated at reflux for 12 h. The precipitated solids were isolated, washed with cold ether and dried, and 29.2 g of a colourless tacky resin were obtained.

N-(2-(2-((Hexylcarbamoyl)oxy)ethoxy)ethyl)-N,N-
dimethylhexadecane-1-aminium bromide (K-30)

To a mixture of 29.4 g of hexyl isocyanate and 0.05 g of Desmorapid Z were added dropwise, at 60° C., 25.6 g of 2-(2-dimethylaminoethoxy)ethanol, and the mixture was kept at this temperature for 8 h. After cooling to room temperature, 50.0 g of aminourethane were obtained.

13.8 g of aminourethane were dissolved in 50 ml of acetonitrile, 162 g of 1-bromohexadecane were added dropwise and the mixture was heated at reflux for 12 h. The precipitated solids were isolated, washed with cold ether and dried, and 25.0 g of colourless solid, m.p. 220-225° C., were obtained.

$N^1,N^{22}$-Dihexadecyl-$N^1,N^1,N^{22},N^{22}$,10,10,13-hep-
tamethyl-7,16-dioxo-3,6,17,20-tetraoxa-8,15-diaz-
adocosane-1,22-diaminiuum dibromide (K-31)

To a mixture of 23.0 g of Vestanat TMDI (product from EVONIK Deutschland) and 0.05 g of Desmorapid Z were added dropwise, at 60° C., 27.9 g of 2-(2-dimethylaminoethoxy)ethanol, and the mixture was kept at this temperature for 8 h. After cooling to room temperature, 50.0 g of aminourethane were obtained.

13.1 g of aminourethane were dissolved in 50 ml of acetonitrile, 16.9 g of 1-bromohexadecane were added dropwise and the mixture was heated at reflux for 12 h. The precipitated solids were isolated, washed with cold ether and dried, and 27.5 g of a colourless tacky resin were obtained.

N-(2-(2-(((3-(10,10-Dimethyl-3-oxo-4,7-dioxa-2,10-
diazahexacosan-10-ium-1-yl)-3,5,5-trimethylcyclo-
hexyl)carbamoyl)oxy)ethoxy)ethyl)-N,N-dimethyl-
hexadecan-1-aminium dibromide (K-32)

To a mixture of 22.7 g of Desmodur I (product from COVESTRO Deutschland) and 0.05 g of Desmorapid Z were added dropwise, at 60° C., 27.2 g of 2-(2-dimethylaminoethoxy)ethanol, and the mixture was kept at this temperature for 8 h. After cooling to room temperature, 50.0 g of aminourethane were obtained.

13.3 g of aminourethane were dissolved in 50 ml of acetonitrile, 16.7 g of 1-bromohexadecane were added dropwise and the mixture was heated at reflux for 12 h. The precipitated solids were isolated, washed with cold ether and dried, and 29.3 g of a colourless tacky resin were obtained.

N,N'-((((((Methylenebis(cyclohexane-4,1-diyl))bis
(azanediyl))bis(carbonyl))bis(oxy))bis(ethane-2,1-
diyl))bis(oxy))bis(ethan-2,1-diyl))bis(N,N-dimethyl-
hexadecane-1-aminium) dibromide (K-33)

To a mixture of 24.8 g of Desmodur W (product from COVESTRO Deutschland) and 0.05 g of Desmorapid Z were added dropwise, at 60° C., 25.2 g of 2-(2-dimethylaminoethoxy)ethanol, and the mixture was kept at this temperature for 8 h. After cooling to room temperature, 50.0 g of aminourethane were obtained.

13.9 g of aminourethane were dissolved in 50 ml of acetonitrile, 16.1 g of 1-bromohexadecane were added dropwise and the mixture was heated at reflux for 12 h. The precipitated solids were isolated, washed with cold ether and dried, and 25.9 g of a colourless tacky resin were obtained.

N,N'-((((((4-Methyl-1,3-phenylene)bis(azanediyl))
bis-(carbonyl))bis(oxy))bis(ethane-2,1-diyl))bis
(oxy))bis(ethane-2,1-diyl))bis(N,N-dimethylhexade-
cane-1-aminium) dibromide (K-34)

To a mixture of 9.90 g of Desmodur T80 (product from COVESTRO Deutschland) and 0.05 g of Desmorapid Z were added dropwise, at 10° C., 15.1 g of 2-(2-dimethylaminoethoxy)ethanol, and, on completion of addition, the mixture was kept at 60° C. for 8 h. After cooling to room temperature, 25.0 g of aminourethane were obtained.

12.6 g of aminourethane were dissolved in 50 ml of acetonitrile, 17.4 g of 1-bromohexadecane were added dropwise and the mixture was heated at reflux for 12 h. The precipitated solids were isolated, washed with cold ether and dried, and 23.1 g of a colourless tacky resin were obtained.

N,N'-((((((Methylenebis(4,1-phenylene))bis
(azanediyl))bis(carbonyl))bis(oxy))bis(ethane-2,1-
diyl))bis(oxy))bis(ethane-2,1-diyl))bis(N,N-dimeth-
ylhexadecane-1-aminium) dibromide (K-35)

To a mixture of 12.1 g of Desmodur MDI (product from COVESTRO Deutschland) and 0.05 g of Desmorapid Z were added dropwise, at 10° C., 12.9 g of 2-(2-dimethylaminoethoxy)ethanol, and, on completion of addition, the mixture was kept at 60° C. for 8 h. After cooling to room temperature, 25.0 g of aminourethane were obtained.

13.8 g of aminourethane were dissolved in 50 ml of acetonitrile, 16.2 g of 1-bromohexadecane were added dropwise and the mixture was heated at reflux for 12 h. The precipitated solids were isolated, washed with cold ether and dried, and 29.4 g of a colourless tacky resin were obtained.

EXAMPLES

Unless noted otherwise, all percentage FIGURES are based on percent by weight.

Preparation Method a1) for Triaryl Organoborates with Cations of Valency n=1

10.0 mmol of the specified boronic ester (I; $R^1$), 30.0 mmol of magnesium turnings and 10.0 mmol of the salt (II) were suspended in a mixture of 3.40 g of anhydrous toluene and 0.73 g of anhydrous tetrahydrofuran in a dry four-neck flask with a mechanical stirrer, thermometer, metal condenser and pressure-equalized dropping funnel under a nitrogen atmosphere, and stirred vigorously for 30 min. The appropriate haloaromatic (III, $R^4$) was added to this solution, at first in undiluted form, until the onset of exothermicity signals the start of the reaction. The remaining total amount of 30.6 mmol of haloaromatic was diluted with 10.0 g of anhydrous toluene and 10.0 g of anhydrous tetrahydrofuran and added dropwise at such a rate that the internal temperature does not exceed 45° C. On completion of addition, the reaction mixture was heated at reflux for 1 h or until the dissolution of the magnesium was complete. The reaction mixture was cooled to room temperature and 100 g of 1,4-dioxane were added dropwise. After standing overnight, the voluminous crystals that had precipitated out were filtered off, the organic phase was concentrated to dryness and the residue was recrystallized from 100 ml of i-propanol. Examples 15, 18, 20 and 27 and 46-52 were isolated without recrystallization as oils with a purity of >90%. The isolated yield for Example 1 that was prepared by this method was 2.87 g (72% of theory), whereas Example 1 prepared according to DE 198 50 139 A1 was obtained in a yield of 47% of theory.

Preparation Method a2) for Triaryl Organoborates with Cations of Valency n=1

10.0 mmol of the specified boronic ester (I; $R^1$), 30.0 mmol of magnesium turnings and 10.0 mmol of the salt (II) were suspended in a mixture of 3.40 g of anhydrous toluene and 0.73 g of anhydrous tetrahydrofuran in a dry four-neck flask with a mechanical stirrer, thermometer, metal condenser and pressure-equalized dropping funnel under a nitrogen atmosphere, and stirred vigorously for 30 min. The appropriate haloaromatic (III, $R^4$) was added to this solution, at first in undiluted form, until the onset of exothermicity signals the start of the reaction. The remaining total amount of 30.6 mmol of haloaromatic was diluted with 10.0 g of anhydrous toluene and 10.0 g of anhydrous tetrahydrofuran and added dropwise at such a rate that the internal temperature does not exceed 45° C. On completion of addition, the reaction mixture was heated at reflux for 1 h or until the dissolution of the magnesium was complete. The reaction mixture was cooled to room temperature and 100 g of Lewatit® MDS TP 208 were added. After 1 h, the resin was filtered off, the organic phase was concentrated to dryness and the residue was recrystallized from 100 ml of i-propanol. Examples 15, 18, 20 and 27 and 46-52 were isolated without recrystallization as oils with a purity of >90%. The isolated yield for Example 1 that was prepared by this method was 2.87 g (72% of theory), whereas Example 1 prepared according to DE 198 50 139 A1 was obtained in a yield of 47% of theory.

The composition of Examples 1-92 and selected physical properties are summarized in Table 2.

TABLE 2

Overview of the compounds of the formula (IV) with n = 1

| | Feedstocks according to preparation method a) | | | Substituents of formula (IV) K⁺ and characterization | | | |
|---|---|---|---|---|---|---|---|
| Example | Boronic ester (I) | Haloaromatic (III) | Salt (II) | $R^1$ | $R^4$ | $^{11}B$ [δ/ppm] | M.p. [° C.] |
| 1 | ethylboronic acid pinacol ester | 1-bromo-4-fluorobenzene | K-1 | ethyl | F—⟨phenyl⟩— | −10.2 | 101-105 |
| 2 | ethylboronic acid pinacol ester | 1-bromo-4-fluorobenzene | K-2 | ethyl | F—⟨phenyl⟩— | −10.3 | 144-149 |
| 3 | ethylboronic acid pinacol ester | 1-bromo-3-chloro-4-methylbenzene | K-1 | ethyl | Cl, Me—⟨phenyl⟩— | −10.3 | 88-91 |
| 4 | ethylboronic acid pinacol ester | 1-bromo-3-chloro-4-methylbenzene | K-2 | ethyl | Cl, Me—⟨phenyl⟩— | −10.2 | 120-122 |
| 5 | isopropylboronic acid pinacol ester | 1-bromo-4-fluorobenzene | K-2 | i-propyl | F—⟨phenyl⟩— | −10.3 | 134-138 |

TABLE 2-continued

Overview of the compounds of the formula (IV) with n = 1

| Example | Feedstocks according to preparation method a) | | | Substituents of formula (IV) K⁺ and characterization | | | |
|---|---|---|---|---|---|---|---|
| | Boronic ester (I) | Haloaromatic (III) | Salt (II) | $R^1$ | $R^4$ | $^{11}B$ [δ/ppm] | M.p. [° C.] |
| 6 | isopropylboronic acid pinacol ester | 1-bromo-3-chloro-4-methylbenzene | K-2 | i-propyl | 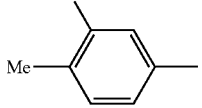 | −8.3 | 115-118 |
| 7 | 2-isopropenyl-boronic acid pinacol ester | 1-bromo-3-chloro-4-methylbenzene | K-2 | 2-propenyl | 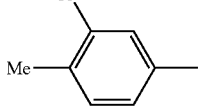 | −8.3 | amorphous |
| 8 | diisopropyl allyl boronate | 1-bromo-3-chloro-4-methylbenzene | K-1 | allyl | 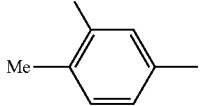 | −10.6 | amorphous |
| 9 | diisopropyl allyl boronate | 1-bromo-3-chloro-4-methylbenzene | K-2 | allyl | 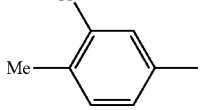 | −10.6 | 84-88 |
| 10 | (1,3,2-dioxaborinan-2-yl)cyclohexane | 1-bromo-4-fluorobenzene | K-1 | cyclohexyl | 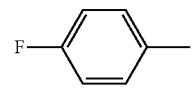 | −10.4 | 59-60 |
| 11 | (1,3,2-dioxaborinan-2-yl)cyclohexane | 1-bromo-4-fluorobenzene | K-2 | cyclohexyl | 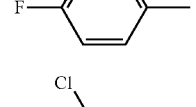 | −10.3 | 166-168 |
| 12 | (1,3,2-dioxaborinan-2-yl)cyclohexane | 1-bromo-3-chloro-4-methylbenzene | K-2 | cyclohexyl | 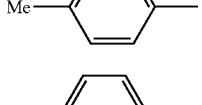 | −8.7 | 175-177 |
| 13 | 2-hexyl-1,3,2-dioxaborinane | 1-bromo-4-fluorobenzene | K-2 | n-hexyl | 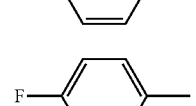 | −10.3 | 59-60 |
| 14 | 1-dodecyl-boronic acid pinacol ester | 1-bromo-4-fluorobenzene | K-2 | n-dodecyl | 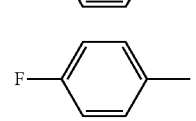 | −10.4 | amorphous |
| 15 | 2-octadecyl-4,4,5,5-tetramethyl-1,3,2-dioxaborolane | 1-bromo-4-fluorobenzene | K-2 | n-octadecyl | 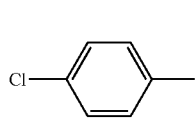 | −10.2 | oil |
| 16 | 2-hexyl-1,3,2-dioxaborinane | 1-bromo-4-chlorobenzene | K-2 | n-hexyl | 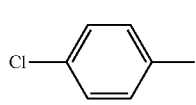 | −10.4 | 80-81 |
| 17 | 1-dodecyl-boronic acid pinacol ester | 1-bromo-4-chlorobenzene | K-2 | n-dodecyl |  | −10.3 | amorphous |

TABLE 2-continued

Overview of the compounds of the formula (IV) with n = 1

| | Feedstocks according to preparation method a) | | | Substituents of formula (IV) K⁺ and characterization | | | |
|---|---|---|---|---|---|---|---|
| Example | Boronic ester (I) | Haloaromatic (III) | Salt (II) | $R^1$ | $R^4$ | $^{11}B$ [δ/ppm] | M.p. [° C.] |
| 18 | 2-octadecyl-4,4,5,5-tetramethyl-1,3,2-dioxaborolane | 1-bromo-4-chlorobenzene | K-2 | n-octadecyl | 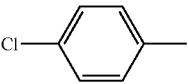 | −10.4 | oil |
| 19 | 2-hexyl-1,3,2-dioxaborinane | 1-bromo-4-trifluoromethyl-benzene | K-2 | n-hexyl | 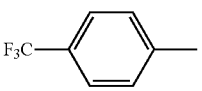 | −9.8 | 80-82 |
| 20 | 2-octadecyl-4,4,5,5-tetramethyl-1,3,2-dioxaborolane | 1-bromo-3-chloro-4-methylbenzene | K-2 | n-octadecyl | 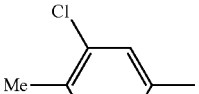 | −10.2 | oil |
| 21 | 3-phenyl-1-propyl-boronic acid pinacol ester | 1-bromo-4-chlorobenzene | K-2 | 3-phenyl propyl | 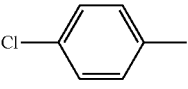 | −10.3 | 101-105 |
| 22 | 3-phenyl-1-propylboronic acid pinacol ester | 1-bromo-4-methoxybenzene | K-2 | 3-phenyl propyl | 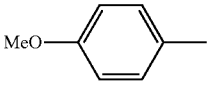 | −10.3 | 116-118 |
| 23 | 3-phenyl-1-propylboronic acid pinacol ester | 1-bromo-3,4,5-trifluorobenzene | K-2 | 3-phenyl propyl | 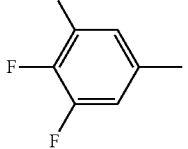 | −10.1 | 78-86 |
| 24 | 3-phenyl-1-propylboronic acid pinacol ester | 1-bromo-3-methyl-4-fluorobenzene | K-2 | 3-phenyl propyl | 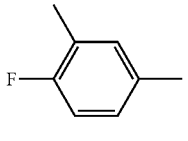 | −13.6 | 85-87 |
| 25 | 3-phenyl-1-propylboronic acid pinacol ester | 1-bromo-4-trifluoromethoxy-benzene | K-2 | 3-phenyl propyl | 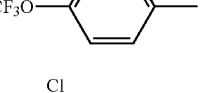 | −10.2 | 101-108 |
| 26 | 2-hexyl-1,3,2-dioxaborinane | 1-bromo-3-chloro-4-methylbenzene | K-3 | n-hexyl | 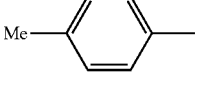 | −10.6 | amorphous |
| 27 | 2-hexyl-1,3,2-dioxaborinane | 1-bromo-3-chloro-4-methylbenzene | K-4 | n-hexyl | 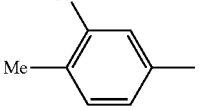 | −10.6 | oil |
| 28 | 2-hexyl-1,3,2-dioxaborinane | 1-bromo-3-chloro-4-methylbenzene | K-5 | n-hexyl | 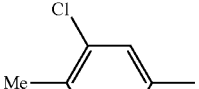 | −10.6 | amorphous |

TABLE 2-continued

Overview of the compounds of the formula (IV) with n = 1

| | Feedstocks according to preparation method a) | | | Substituents of formula (IV) K⁺ and characterization | | | |
|---|---|---|---|---|---|---|---|
| Example | Boronic ester (I) | Haloaromatic (III) | Salt (II) | $R^1$ | $R^4$ | $^{11}B$ [δ/ppm] | M.p. [° C.] |
| 29 | 2-hexyl-1,3,2-dioxaborinane | 1-bromo-3-chloro-4-methylbenzene | K-6 | n-hexyl | 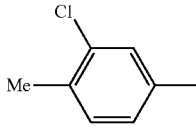 | −10.6 | amorphous |
| 30 | 2-hexyl-1,3,2-dioxaborinane | 1-bromo-3-chloro-4-methylbenzene | K-7 | n-hexyl | 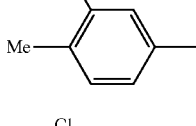 | −10.6 | amorphous |
| 31 | 2-hexyl-1,3,2-dioxaborinane | 1-bromo-3-chloro-4-methylbenzene | K-8 | n-hexyl | 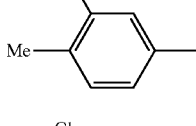 | −10.6 | amorphous |
| 32 | 2-hexyl-1,3,2-dioxaborinane | 1-bromo-3-chloro-4-methylbenzene | K-9 | n-hexyl | 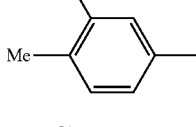 | −10.6 | amorphous |
| 33 | 2-hexyl-1,3,2-dioxaborinane | 1-bromo-3-chloro-4-methylbenzene | K-10 | n-hexyl | 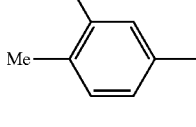 | −10.6 | amorphous |
| 34 | 2-hexyl-1,3,2-dioxaborinane | 1-bromo-3-chloro-4-methylbenzene | K-11 | n-hexyl | 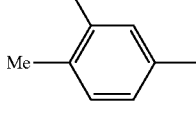 | −10.6 | amorphous |
| 35 | 2-hexyl-1,3,2-dioxaborinane | 1-bromo-3-chloro-4-methylbenzene | K-12 | n-hexyl | 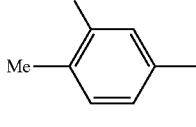 | −10.6 | amorphous |
| 36 | 2-hexyl-1,3,2-dioxaborinane | 1-bromo-3-chloro-4-methylbenzene | K-13 | n-hexyl | 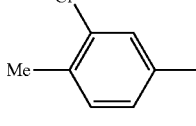 | −10.6 | amorphous |
| 37 | 2-hexyl-1,3,2-dioxaborinane | 1-bromo-3-chloro-4-methylbenzene | K-16 | n-hexyl | 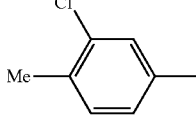 | −10.6 | amorphous |
| 38 | 2-hexyl-1,3,2-dioxaborinane | 1-bromo-3-chloro-4-methylbenzene | K-17 | n-hexyl | 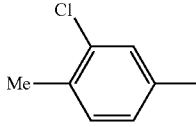 | −10.6 | amorphous |

TABLE 2-continued

Overview of the compounds of the formula (IV) with n = 1

| | Feedstocks according to preparation method a) | | | Substituents of formula (IV) K⁺ and characterization | | | |
|---|---|---|---|---|---|---|---|
| Example | Boronic ester (I) | Haloaromatic (III) | Salt (II) | $R^1$ | $R^4$ | $^{11}B$ [δ/ppm] | M.p. [° C.] |
| 39 | 2-hexyl-1,3,2-dioxaborinane | 1-bromo-3-chloro-4-methylbenzene | K-19 | n-hexyl | 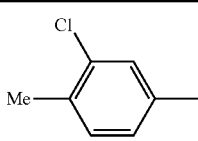 | −10.6 | amorphous |
| 40 | 2-hexyl-1,3,2-dioxaborinane | 1-bromo-3-chloro-4-methylbenzene | K-20 | n-hexyl | 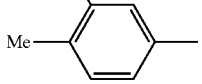 | −10.6 | amorphous |
| 41 | 2-hexyl-1,3,2-dioxaborinane | 1-bromo-3-chloro-4-methylbenzene | K-21 | n-hexyl | 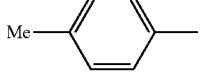 | −10.6 | amorphous |
| 42 | 2-hexyl-1,3,2-dioxaborinane | 1-bromo-3-chloro-4-methylbenzene | K-22 | n-hexyl | 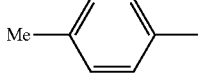 | −10.6 | amorphous |
| 43 | 2-hexyl-1,3,2-dioxaborinane | 1-bromo-3-chloro-4-methylbenzene | K-23 | n-hexyl | 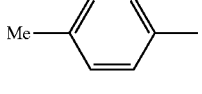 | −10.6 | amorphous |
| 44 | 2-hexyl-1,3,2-dioxaborinane | 1-bromo-3-chloro-4-methylbenzene | K-24 | n-hexyl | 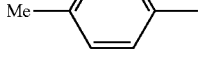 | −10.6 | amorphous |
| 45 | 2-hexyl-1,3,2-dioxaborinane | 1-bromo-3-chloro-4-methylbenzene | K-30 | n-hexyl | 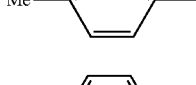 | −10.6 | amorphous |
| 46 | 1-dodecyl-boronic acid pinacol ester | 1-bromo-4-chlorobenzene | K-2 | n-dodecyl | 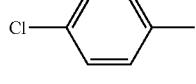 | −10.3 | oil |
| 47 | 1-dodecyl-boronic acid pinacol ester | 1-bromo-4-methoxybenzene | K-2 | n-dodecyl | 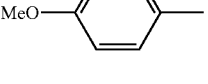 | −10.4 | oil |
| 48 | 1-dodecyl-boronic acid pinacol ester | 1-bromo-3,4,5-trifluorobenzene | K-2 | n-dodecyl | 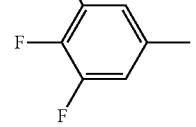 | −10.1 | oil |

TABLE 2-continued

Overview of the compounds of the formula (IV) with n = 1

| | Feedstocks according to preparation method a) | | | Substituents of formula (IV) K$^+$ and characterization | | | |
|---|---|---|---|---|---|---|---|
| Example | Boronic ester (I) | Haloaromatic (III) | Salt (II) | R$^1$ | R$^4$ | $^{11}$B [δ/ppm] | M.p. [° C.] |
| 49 | 1-dodecyl-boronic acid pinacol ester | 1-bromo-3-methyl-4-fluorobenzene | K-2 | n-dodecyl | 3-F, 4-Me-phenyl | −10.6 | oil |
| 50 | 1-dodecyl-boronic acid pinacol ester | 1-bromo-4-trifluoromethoxy-benzene | K-2 | n-dodecyl | 4-CF$_3$O-phenyl | −10.8 | oil |
| 51 | 2-hexyl-1,3,2-dioxaborinane | 1-bromo-3-chloro-4-methylbenzene | K-100 | n-hexyl | 3-Cl, 4-Me-phenyl | −10.6 | oil |
| 52 | 2-hexyl-1,3,2-dioxaborinane | 1-bromo-3-chloro-4-methylbenzene | K-101 | n-hexyl | 3-Cl, 4-Me-phenyl | −10.6 | oil |
| 53 | 2-hexyl-1,3,2-dioxaborinane | 1-bromo-3-chloro-4-methylbenzene | K-102 | n-hexyl | 3-Cl, 4-Me-phenyl | −10.6 | decomp. |
| 54 | 2-hexyl-1,3,2-dioxaborinane | 1-bromo-3-chloro-4-methylbenzene | K-103 | n-hexyl | 3-Cl, 4-Me-phenyl | −10.6 | 102-105 |
| 55 | 2-hexyl-1,3,2-dioxaborinane | 1-bromo-3-chloro-4-methylbenzene | K-104 | n-hexyl | 3-Cl, 4-Me-phenyl | −10.6 | 134-138 |
| 56 | 2-hexyl-1,3,2-dioxaborinane | 1-bromo-3-chloro-4-methylbenzene | K-105 | n-hexyl | 3-Cl, 4-Me-phenyl | −10.6 | 145-146 |
| 57 | 2-hexyl-1,3,2-dioxaborinane | 1-bromo-3-chloro-4-methylbenzene | K-106 | n-hexyl | 3-Cl, 4-Me-phenyl | −10.6 | 155-159 |
| 58 | 2-hexyl-1,3,2-dioxaborinane | 1-bromo-3-chloro-4-methylbenzene | K-200 | n-hexyl | 3-Cl, 4-Me-phenyl | −10.4 | amorphous |

TABLE 2-continued

Overview of the compounds of the formula (IV) with n = 1

| | Feedstocks according to preparation method a) | | | Substituents of formula (IV) K⁺ and characterization | | | |
|---|---|---|---|---|---|---|---|
| Example | Boronic ester (I) | Haloaromatic (III) | Salt (II) | R$^1$ | R$^4$ | $^{11}$B [δ/ppm] | M.p. [° C.] |
| 59 | 2-hexyl-1,3,2-dioxaborinane | 1-bromo-3-chloro-4-methylbenzene | K-201 | n-hexyl | 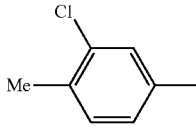 | −10.4 | amorphous |
| 60 | 2-hexyl-1,3,2-dioxaborinane | 1-bromo-3-chloro-4-methylbenzene | K-202 | n-hexyl | 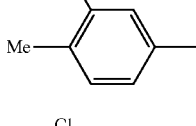 | −10.4 | amorphous |
| 61 | 2-hexyl-1,3,2-dioxaborinane | 1-bromo-3-chloro-4-methylbenzene | K-300 | n-hexyl | 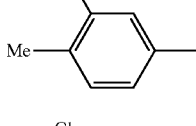 | −10.6 | amorphous |
| 62 | 2-hexyl-1,3,2-dioxaborinane | 1-bromo-3-chloro-4-methylbenzene | K-303 | n-hexyl | 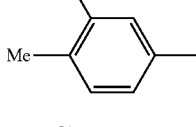 | −10.6 | amorphous |
| 63 | 2-hexyl-1,3,2-dioxaborinane | 1-bromo-3-chloro-4-methylbenzene | K-303 | n-hexyl | 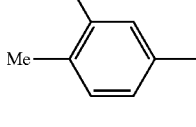 | −10.6 | amorphous |
| 64 | 2-hexyl-1,3,2-dioxaborinane | 1-bromo-3-chloro-4-methylbenzene | K-304 | n-hexyl | 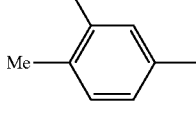 | −10.6 | amorphous |
| 65 | 2-hexyl-1,3,2-dioxaborinane | 1-bromo-3-chloro-4-methylbenzene | K-305 | n-hexyl | 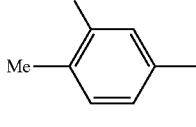 | −10.6 | amorphous |
| 66 | 2-hexyl-1,3,2-dioxaborinane | 1-bromo-3-chloro-4-methylbenzene | K-400 | n-hexyl | 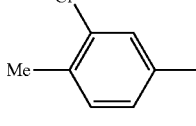 | −10.5 | amorphous |
| 67 | 2-hexyl-1,3,2-dioxaborinane | 1-bromo-3-chloro-4-methylbenzene | K-401 | n-hexyl | 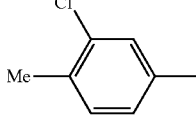 | −10.5 | amorphous |
| 68 | 2-hexyl-1,3,2-dioxaborinane | 1-bromo-3-chloro-4-methylbenzene | K-402 | n-hexyl | 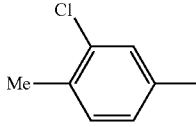 | −10.5 | amorphous |

TABLE 2-continued

Overview of the compounds of the formula (IV) with n = 1

| | Feedstocks according to preparation method a) | | | Substituents of formula (IV) K⁺ and characterization | | | |
|---|---|---|---|---|---|---|---|
| Example | Boronic ester (I) | Haloaromatic (III) | Salt (II) | $R^1$ | $R^4$ | $^{11}B$ [δ/ppm] | M.p. [° C.] |
| 69 | 2-hexyl-1,3,2-dioxaborinane | 1-bromo-3-chloro-4-methylbenzene | K-403 | n-hexyl | 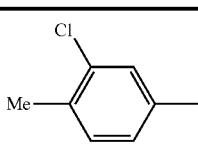 | −10.5 | amorphous |
| 86 | 2-hexyl-1,3,2-dioxaborinane | 1-bromo-3-chloro-4-methylbenzene | K-37 | n-hexyl | 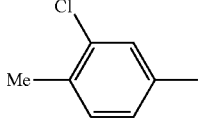 | −10.5 | amorphous |
| 87 | 2-hexyl-1,3,2-dioxaborinane | 1-bromo-3-chloro-4-methylbenzene | K-38 | n-hexyl | 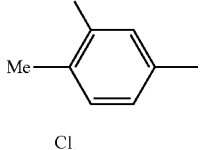 | −10.5 | amorphous |
| 88 | 2-hexyl-1,3,2-dioxaborinane | 1-bromo-3-chloro-4-methylbenzene | K-39 | n-hexyl | 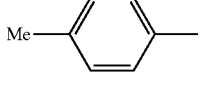 | −10.5 | amorphous |
| 89 | 2-hexyl-1,3,2-dioxaborinane | 1-bromo-3-chloro-4-methylbenzene | K-40 | n-hexyl | 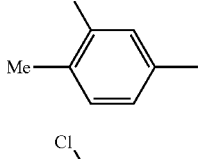 | −10.5 | amorphous |
| 90 | 2-hexyl-1,3,2-dioxaborinane | 1-bromo-3-chloro-4-methylbenzene | K-41 | n-hexyl | 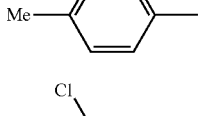 | −10.5 | amorphous |
| 91 | 2-hexyl-1,3,2-dioxaborinane | 1-bromo-3-chloro-4-methylbenzene | K-42 | n-hexyl | 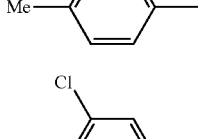 | −10.5 | amorphous |
| 92 | 2-hexyl-1,3,2-dioxaborinane | 1-bromo-3-chloro-4-methylbenzene | K-43 | n-hexyl | 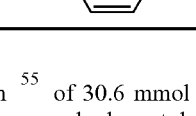 | −10.5 | amorphous |

Preparation Method b1) for Triaryl Organoborates with Cations of Valency n=2

10.0 mmol of the specified boronic ester (I; $R^1$), 30.0 mmol of magnesium turnings and 5.0 mmol of the salt (II) were suspended in a mixture of 3.40 g of anhydrous toluene and 0.73 g of anhydrous tetrahydrofuran in a dry four-neck flask with a mechanical stirrer, thermometer, metal condenser and pressure-equalized dropping funnel under a nitrogen atmosphere, and stirred vigorously for 30 min. The appropriate haloaromatic (III, $R^4$) was added to this solution, at first in undiluted form, until the onset of exothermicity signals the start of the reaction. The remaining total amount of 30.6 mmol of haloaromatic was diluted with 10.0 g of anhydrous toluene and 10.0 g of anhydrous tetrahydrofuran and added dropwise at such a rate that the internal temperature does not exceed 45° C. On completion of addition, the reaction mixture was heated at reflux for 1 h or until the dissolution of the magnesium was complete. The reaction mixture was cooled to room temperature and 100 g of 1,4-dioxane were added dropwise. After standing overnight, the voluminous crystals that had precipitated out were filtered off, the organic phase was concentrated to dryness and the residue was recrystallized from 100 ml of i-propanol.

Preparation Method b2) for Triaryl Organoborates with Cations of Valency n=2

10.0 mmol of the specified boronic ester (I; $R^1$), 30.0 mmol of magnesium turnings and 5.0 mmol of the salt (II) were suspended in a mixture of 3.40 g of anhydrous toluene and 0.73 g of anhydrous tetrahydrofuran in a dry four-neck flask with a mechanical stirrer, thermometer, metal condenser and pressure-equalized dropping funnel under a nitrogen atmosphere, and stirred vigorously for 30 min. The appropriate haloaromatic (III, $R^4$) was added to this solution, at first in undiluted form, until the onset of exothermicity signals the start of the reaction. The remaining total amount of 30.6 mmol of haloaromatic was diluted with 10.0 g of anhydrous toluene and 10.0 g of anhydrous tetrahydrofuran and added dropwise at such a rate that the internal temperature does not exceed 45° C. On completion of addition, the reaction mixture was heated at reflux for 1 h or until the dissolution of the magnesium was complete. The reaction mixture was cooled to room temperature and 100 g of Lewatit® MDS TP 208 were added. After 1 h, the resin was filtered off, the organic phase was concentrated to dryness and the residue was recrystallized from 100 ml of i-propanol.

The composition of Examples 93-107 and selected physical properties are summarized in Table 3.

TABLE 3

Overview of the compounds of the formula (IV) with n = 2

| | Feedstocks according to preparation method b1) & b2) | | | Substituents of formula (IV) $K^+$ and characterization | | | |
|---|---|---|---|---|---|---|---|
| Example | Boronic ester (I) | Haloaromatic (III) | Salt (II) | $R^1$ | $R^4$ | $^{11}B$ [δ/ppm] | M.p. [° C.] |
| 93 | 2-hexyl-1,3,2-dioxaborinane | 1-bromo-3-chloro-4-methylbenzene | K-14 | n-hexyl | 3-chloro-4-methylphenyl | −10.6 | amorphous |
| 94 | 2-hexyl-1,3,2-dioxaborinane | 1-bromo-3-chloro-4-methylbenzene | K-15 | n-hexyl | 3-chloro-4-methylphenyl | −10.6 | amorphous |
| 95 | 2-hexyl-1,3,2-dioxaborinane | 1-bromo-3-chloro-4-methylbenzene | K-18 | n-hexyl | 3-chloro-4-methylphenyl | −10.6 | amorphous |
| 96 | 2-hexyl-1,3,2-dioxaborinane | 1-bromo-3-chloro-4-methylbenzene | K-25 | n-hexyl | 3-chloro-4-methylphenyl | −10.6 | amorphous |
| 97 | 2-hexyl-1,3,2-dioxaborinane | 1-bromo-3-chloro-4-methylbenzene | K-26 | n-hexyl | 3-chloro-4-methylphenyl | −10.6 | amorphous |
| 98 | 2-hexyl-1,3,2-dioxaborinane | 1-bromo-3-chloro-4-methylbenzene | K-27 | n-hexyl | 3-chloro-4-methylphenyl | −10.6 | amorphous |
| 99 | 2-hexyl-1,3,2-dioxaborinane | 1-bromo-3-chloro-4-methylbenzene | K-28 | n-hexyl | 3-chloro-4-methylphenyl | −10.6 | amorphous |
| 100 | 2-hexyl-1,3,2-dioxaborinane | 1-bromo-3-chloro-4-methylbenzene | K-29 | n-hexyl | 3-chloro-4-methylphenyl | −10.6 | amorphous |

TABLE 3-continued

Overview of the compounds of the formula (IV) with n = 2

| | Feedstocks according to preparation method b1) & b2) | | | Substituents of formula (IV) K+ and characterization | | | |
|---|---|---|---|---|---|---|---|
| Example | Boronic ester (I) | Haloaromatic (III) | Salt (II) | R¹ | R⁴ | ¹¹B [δ/ppm] | M.p. [° C.] |
| 101 | 2-hexyl-1,3,2-dioxaborinane | 1-bromo-3-chloro-4-methylbenzene | K-31 | n-hexyl | 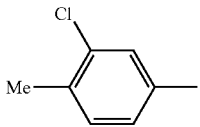 | −10.6 | amorphous |
| 102 | 2-hexyl-1,3,2-dioxaborinane | 1-bromo-3-chloro-4-methylbenzene | K-32 | n-hexyl | 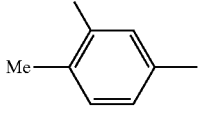 | −10.6 | amorphous |
| 103 | 2-hexyl-1,3,2-dioxaborinane | 1-bromo-3-chloro-4-methylbenzene | K-33 | n-hexyl | 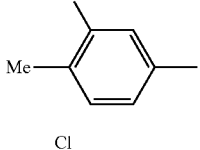 | −10.6 | amorphous |
| 104 | 2-hexyl-1,3,2-dioxaborinane | 1-bromo-3-chloro-4-methylbenzene | K-34 | n-hexyl | 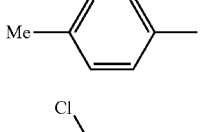 | −10.6 | amorphous |
| 105 | 2-hexyl-1,3,2-dioxaborinane | 1-bromo-3-chloro-4-methylbenzene | K-35 | n-hexyl | 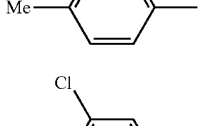 | −10.6 | amorphous |
| 106 | 2-hexyl-1,3,2-dioxaborinane | 1-bromo-3-chloro-4-methylbenzene | K-203 | n-hexyl | 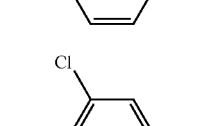 | −10.5 | amorphous |
| 107 | 2-hexyl-1,3,2-dioxaborinane | 1-bromo-3-chloro-4-methylbenzene | K-301 | n-hexyl | 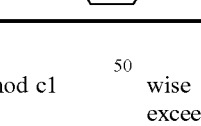 | −10.6 | amorphous |

Example 108 (Cation of Valency n=3), Method c1

1.70 g of 2-hexyl-1,3,2-dioxaborinane (10.0 mmol; I; R¹=n-hexyl), 0.73 g (30.0 mmol) of magnesium turnings and 2.25 g of $N^1,N^1,N^1,N^3,N^3,N^3,N^5,N^5,N^5$-nonamethyl-1,3,5-benzentrimethanaminium triiodide (3.33 mmol; K-36; II) are suspended in a mixture of 3.40 g of anhydrous toluene and 0.73 g of anhydrous tetrahydrofuran in a dry four-neck flask having a mechanical stirrer, thermometer, metal condenser and pressure-equalized dropping funnel under a nitrogen atmosphere, and stirred vigorously for 30 min. 1-Bromo-3-chloro-4-methylbenzene (III, R⁴) is added to this solution, at first in undiluted form, until the onset of exothermicity signals the start of the reaction. The remaining total amount of 6.29 g (30.6 mmol) of 1-bromo-3-chloro-4-methylbenzene is diluted with 10.0 g of anhydrous toluene and 10.0 g of anhydrous tetrahydrofuran and added dropwise at such a rate that the internal temperature does not exceed 45° C. On completion of addition, the reaction mixture is heated at reflux for 1 h or until the dissolution of the magnesium was complete. The reaction mixture was cooled to room temperature and 100 g of 1,4-dioxane were added dropwise. After standing overnight, the voluminous crystals that had precipitated out were filtered off, the organic phase was concentrated to dryness and the residue was recrystallized from 100 ml of i-propanol.

$^{11}$B NMR [δ/ppm]−10.6.

Example 108 (Cation of Valency n=3), Method c2

1.70 g of 2-hexyl-1,3,2-dioxaborinane (10.0 mmol; I; R¹=n-hexyl), 0.73 g (30.0 mmol) of magnesium turnings and 2.25 g of $N^1,N^1,N^1,N^3,N^3,N^3,N^5,N^5,N^5$-nonamethyl-1,3,5-benzentrimethanaminium II) are suspended in a mixture of 3.40 g of anhydrous toluene and 0.73 g of anhydrous tetrahydrofuran in a dry four-neck flask having a mechanical stirrer, thermometer, metal condenser and pressure-equalized dropping funnel under a nitrogen atmosphere, and stirred vigorously for 30 min. 1-Bromo-3-chloro-4-methylbenzene (III, $R^4$) is added to this solution, at first in undiluted form, until the onset of exothermicity signals the start of the reaction. The remaining total amount of 6.29 g (30.6 mmol) of 1-bromo-3-chloro-4-methylbenzene is diluted with 10.0 g of anhydrous toluene and 10.0 g of anhydrous tetrahydrofuran and added dropwise at such a rate that the internal temperature does not exceed 45° C. On completion of addition, the reaction mixture is heated at reflux for 1 h or until the dissolution of the magnesium was complete. The reaction mixture was cooled to room temperature and 100 g of Lewatit® MDS TP 208 were added. After 1 h, the resin was filtered off, the organic phase was concentrated to dryness and the residue was recrystallized from 100 ml of i-propanol.

$^{11}$B NMR [δ/ppm]–10.6.

Production of Media to Determine the Holographic Properties

Example Medium I 3.38 g of the polyol component 1 were mixed with 0.010 g of Example 1, 2.00 g of urethane acrylate 1, 2.00 g of urethane acrylate 2, 1.50 g of additive 1, 0.10 g of triaryl alkyl borate 1 of formula (IV), 0.010 g of dye 1 and 0.35 g of N-ethylpyrrolidone at 60° C., so as to obtain a clear solution. Subsequently, the mixture was cooled down to 30° C., 0.65 g of Desmodur® N3900 was added and the mixture was mixed again. Finally, 0.01 g of Fomrez UL 28 was added and the mixture was mixed briefly again. The fluid mass obtained was then applied to a glass plate and covered thereon with a second glass plate. This specimen was left to stand at room temperature for 12 hours and hardened.

Example Medium II-XX

The procedure was as in Example medium I, except using 0.10 g of the specified triaryl organoborate of formula (IV) rather than 0.10 g of triaryl organoborate 1.

The properties of Example media I-XX are summarized in Table 4.

TABLE 4

Overview of the holographic properties of Example media I-XX

| Example medium | Example of formula (IV) | Δn |
|---|---|---|
| I | 1 | 0.033 |
| II | 13 | 0.029 |
| III | 16 | 0.029 |
| IV | 17 | 0.034 |
| V | 18 | 0.033 |
| VI | 19 | 0.032 |
| VII | 20 | 0.037 |
| VIII | 24 | 0.033 |
| IX | 29 | 0.034 |
| X | 45 | 0.039 |
| XI | 51 | 0.035 |
| XII | 52 | 0.034 |
| XIII | 57 | 0.037 |
| XIV | 66 | 0.038 |
| XV | 93 | 0.037 |
| XVI | 95 | 0.040 |
| XVII | 97 | 0.040 |
| XVIII | 101 | 0.037 |
| XIX | 102 | 0.035 |
| XX | 104 | 0.037 |

The values found for Example media I to XX show that the compounds of the formula (IV) used in the photopolymer formulations are of very good suitability for use in holographic media.

The invention claimed is:

1. Process for preparing triaryl organoborates of the formula 1/n $K^{n+}R_3^4B^−$—$R^1$ (IV), where one equivalent of organoboronic ester of the formula B—$R^1(OR^2)(OR^3)$ (I) is initially charged together with 1/n equivalents of salt $K^{n+}$ $nX^−$ (II) and 3 equivalents of metal M in a solvent or a solvent mixture S1, 3 equivalents of a haloaromatic $R^4$—Y (III) are added, an auxiliary L and optionally a second organic solvent or solvent mixture S2 is added and the compound 1/n $K^{n+}$ $R_3^{4B}B^−$—$R^1$ (IV) is separated off with the organic phase and $R^1$ is an optionally hydroxyl- and/or alkoxy- and/or acyloxy- and/or halogen-substituted $C_1$- to $C_{22}$-alkyl, $C_3$- to $C_{22}$-alkenyl, $C_3$- to $C_{22}$-alkynyl, $C_5$- to $C_7$-cycloalkyl or $C_7$- to $C_{13}$-aralkyl radical, $R^2$ and $R^3$ are independently an optionally branched $C_1$- to $C_{22}$-alkyl radical or an optionally alkyl-substituted $C_3$- to $C_7$-cycloalkyl radical or $R^2$ and $R^3$ together form a 2-8-membered carbon bridge which is optionally substituted by alkyl and/or interrupted by oxygen atoms, or $R^2$ and $R^3$ together form a 4-7-membered, optionally substituted, carbocycle, $R^4$ is a $C_6$- to $C_{10}$-aryl radical optionally substituted by at least one radical selected from halogen, $C_1$- to $C_4$-alkyl, trifluoromethyl, $C_1$- to $C_4$-alkoxy, trifluoromethoxy, phenyl and phenoxy, K is an organocation of valency n and having any substitution, based on nitrogen, phosphorus, oxygen, sulfur and/or iodine, and L is an auxiliary that forms a complex of sparing solubility in S1 and/or S2 with M salts $MY(OR^2)$, $MY(OR^3)$ and MXY, where L is a Lewis-basic compound, selected from the group consisting of open chain or cyclic or polycyclic ethers or polyethers or (poly)ether polyols, amine-functionalized and/or alkanolamine-functionalized alcohols or polyols or (poly)ether polyols, weakly basic organic compounds, weakly acidic macroporous cation exchangers and weakly alkaline macroporous cation exchangers, M is any metal selected from the alkali metals, or from magnesium, calcium and aluminium, X is a halide or alkoxide or alkyl sulfide, Y is iodine or bromine or chlorine, n is 1, 2 or 3, S1 is an aprotic organic solvent or a mixture of aprotic solvents and S2 is an aprotic organic solvent or a mixture of aprotic solvents.

2. Process for preparing compounds 1/n $K^{n+}$ $R_3^4B^−$—$R^1$ of the formula IV according to claim 1, comprising the steps of i) initially charging one equivalent of organoboronic ester B—$R^1(OR^2)(OR^3)$ (I) together with 1/n equivalents of salt $K^{n+}$ $nX^-$ (II) and 3 equivalents of metal M in a solvent or solvent mixture S1, ii) adding 3 equivalents of a haloaromatic $R^4$—Y (III), as a result of which iii) an organometallic reagent generated in situ reacts with the initially charged substances (I) and (II) to give 1/n $K^{n+}$ $R_3^4B^-$—$R^1$ (IV), iv) adding an auxiliary L and v) optionally a second organic solvent S2, where the compound (IV) remains in the organic phase, and vi) the metal salts $MY(OR^2)$, $MY(OR^3)$ and MXY are separated off as precipitated solid complexes $MY(OR^2)$L, $MY(OR^3)$L and MXYL.

3. Process according to claim 1, characterized in that the auxiliary L comprises Lewis-basic compounds having at least one freely available coordination site or mixtures thereof, selected from the group consisting of open-chain or cyclic or polycyclic ethers or polyethers or (poly)ether polyols, amine- and/or alkylamine-functionalized alcohols or polyols or (poly)ether polyols, weakly basic organic compounds, weakly acidic macroporous cation exchangers and weakly alkaline macroporous cation exchangers.

4. Process according to claim 1, characterized in that the solvent or solvent mixtures S1 and S2 are independently anhydrous aprotic organic solvents or mixtures thereof.

5. Process according to claim 1, characterized in that the organocations K of valency n based on nitrogen are ammonium ions, pyridinium ions, pyridazinium ions, pyrimidinium ions, pyrazinium ions, imidazolium ions, pyrrolidinium ions, which optionally bear further functional groups selected from the group consisting of ethers, esters, amides and carbamates in one or more side chains and which may also be in oligomeric or polymeric or bridging form.

6. Process according to claim 1, characterized in that the organocations K of valency n based on phosphorus are tetraalkylphosphonium, trialkylarylphosphonium, dialkyldiarylphosphonium, alkyltriarylphosphonium or tetraarylphosphonium salts having any substitution, which optionally bear further functional groups selected from the group consisting of carbonyls, amides and carbamates in one or more side chains and which may also be in oligomeric or polymeric or bridging form.

7. Process according to claim 1, characterized in that the organocation K of valency n based on oxygen is pyrylium having any substitution, including in fused form as in benzopyrylium, flavylium, naphthoxanthenium or polymeric cations.

8. Process according to claim 1, characterized in that the organocations K of valency n based on sulfur are onium compounds of sulfur that bear identical or different optionally substituted $C_4$- to $C_{14}$-alkyl, $C_6$- to $C_{10}$-aryl, $C_7$- to $C_{12}$-arylalkyl or $C_5$- to $C_6$-cycloalkyl radicals and/or that form oligomeric or polymeric repeating connecting units to give sulfonium salts with $1 \leq n \leq 3$, and thiopyrylium or polymeric cations.

9. Process according to claim 1, characterized in that the organocations K of valency n based on iodine are onium compounds of iodine bearing identical or different optionally substituted $C_1$- to $C_{22}$-alkyl, $C_6$- to $C_{14}$-aryl, $C_7$- to $C_{15}$-arylalkyl or $C_5$- to $C_7$-cycloalkyl radicals and/or form oligomeric or polymeric repeating connecting units to give iodonium salts with $1 \leq n \leq 3$, or are further polymeric cations.

10. Process according to claim 1, characterized in that $R^1$ is an optionally hydroxyl- and/or alkoxy- and/or acyloxy- and/or halogen-substituted $C_2$- to $C_{18}$-alkyl, $C_3$- to $C_{18}$-alkenyl, $C_3$- to $C_{18}$-alkynyl, $C_5$- to $C_6$-cycloalkyl or $C_7$- to $C_{13}$-aralkyl radical.

11. Process according to claim 1, characterized in that $R^2$ and $R^3$ are independently an optionally branched $C_2$- to $C_{18}$-alkyl radical or $R^2$ and $R^3$ together form a 4-7-membered, optionally substituted carbocycle.

12. Process according to claim 1, characterized in that $R^4$ is a $C_6$- to $C_{10}$-aryl radical optionally substituted by at least one radical selected from halogen, $C_1$- to $C_4$-alkyl, trifluoromethyl, $C_1$- to $C_4$-alkoxy, trifluoromethoxy, phenyl and/or phenoxy.

\* \* \* \* \*